United States Patent
Gong et al.

(10) Patent No.: US 6,670,150 B1
(45) Date of Patent: Dec. 30, 2003

(54) ISOLATED HUMAN RECEPTOR PROTEINS, NUCLEIC ACID MOLECULES ENCODING HUMAN RECEPTOR PROTEINS, AND USES THEREOF

(75) Inventors: Fangcheng Gong, Germantown, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 44 days.

(21) Appl. No.: 09/851,985

(22) Filed: May 10, 2001

(51) Int. Cl.$^7$ .................. C07K 14/705; C12N 15/12
(52) U.S. Cl. .............. 435/69.1; 435/252.3; 435/320.1; 530/350; 536/23.5
(58) Field of Search ................ 435/69.1, 252.3, 435/320.1; 530/350; 536/23.5

(56) References Cited

PUBLICATIONS

Prevost et al. Determinants of the Functional Interaction Between the Soluble GM–CSF Receptor and the GM–CSF Receptor beta–Subunit. Mar. 2000. CYTOKINE 12(3):187–197.*

Hayashida et al. Molecular Cloning of a Second Subunit of the Receptor for Human Granulocyte–Macrophage Colony–Stimulating Factor (GM–CSF): Reconstitution of a High–Affinity GM–CSF Receptor. Dec. 1990. P.N.A.S. 87:9655–9659.*

McCormack et al. Novel Murine Myeloid Cell Lines that Exhibit a Differentiation Switch in Response to IL–3 or GM–CSF, or to Different Constitutively Active Mutants of the GM–CSF Receptor beta Subunit. Jan. 2000. Blood 95(1):120–127.*

* cited by examiner

*Primary Examiner*—John Ulm
(74) *Attorney, Agent, or Firm*—Celera Genomics; Justin D. Karjala

(57) ABSTRACT

The present invention provides amino acid sequences of peptides that are encoded by genes within the human genome, the receptor peptides of the present invention. The present invention specifically provides isolated peptide and nucleic acid molecules, methods of identifying orthologs and paralogs of the receptor peptides, and methods of identifying modulators of the receptor peptides.

9 Claims, 17 Drawing Sheets

```
   1 CTCCCACCAC ACAGAGGCCT GGAGGAGGCA GAGGCCAGGA GGGAGAGGTC
  51 CCAAGAGCCT GTGAAATGGG TCTGGCCTGG CTCCCAGCTG GGCAGGAACA
 101 CAGGACTTCA GGATACTAAG GACCCTGTCA TGCCCATGGC CAGCACCCAC
 151 CAGTGCTGGT GCCTGCCTGT CCAGAGCTGA CCAGGGAGAT GGTGCTGGCC
 201 CAGGGGCTGC TCTCCATGGC CCTGCTGGCC CTGTGCTGGG AGCGCAGCCT
 251 GGCAGGGGCA GAAGAAACCA TCCCGCTGCA GACCCTGCGC TGCTACAACG
 301 ACTACACCAG CCACATCACC TGCAGGTGGG CAGACACCCA GGATGCCCAG
 351 CGGCTCGTCA ACGTGACCCT CATTCGCCGG GTGAATGAGG ACCTCCTGGA
 401 GCCAGTGTCC TGTGACCTCA GTGATGACAT GCCCTGGTCA GCCTGCCCCC
 451 ATCCCCGCTG CGTGCCCAGG AGATGTGTCA TTCCCTGCCA GAGTTTTGTC
 501 GTCACTGACG TTGACTACTT CTCATTCCAA CCAGACAGGC CTCTGGGCAC
 551 CCGGCTCACC GTCACTCTGA CCCAGCATGT CCAGCCTCCT GAGCCCAGGG
 601 ACCTGCAGAT CAGCACCGAC CAGGACCACT TCCTGCTGAC CTGGAGTGTG
 651 GCCCTTGGGA GTCCCCAGAG CCACTGGTTG TCCCCAGGGG ATCTGGAGTT
 701 TGAGGTGGTC TACAAGCGGC TTCAGGACTC TTGGGAGGAC GCAGCCATCC
 751 TCCTCTCCAA CACCTCCCAG GCCACCCTGG GGCCAGAGCA CCTCATGCCC
 801 AGCAGCACCT ACGTGGCCCG AGTACGGACC CGCCTGGCCC CAGGTTCTCG
 851 GCTCTCAGGA CGTCCCAGCA AGTGGAGCCC AGAGGTTTGC TGGGACTCCC
 901 AGCCAGGGGA TGAGGCCCAG CCCCAGAACC TGGAGTGCTT CTTTGACGGG
 951 GCCGCCGTGC TCAGCTGCTC CTGGGAGGTG AGGAAGGAGG TGGCCAGCTC
1001 GGTCTCCTTT GGCCTATTCT ACAAGCCCAG CCCAGATGCA GGGGAGGAAG
1051 AGTGCTCCCC AGTGCTGAGG GAGGGGCTCG GCAGCCTCCA CACCAGGCAC
1101 CACTGCCAGA TTCCCGTGCC CGACCCCGCG ACCCACGGCC AATACATCGT
1151 CTCTGTTCAG CCAAGGAGGG CAGAGAAACA CATAAAGAGC TCAGTGAACA
1201 TCCAGATGGC CCCTCCATCC CTCAACGTGA CCAAGGATGG AGACAGCTAC
1251 AGCCTGCGCT GGGAAACAAT GAAAATGCGA TACGAACACA TAGACCACAC
1301 ATTTGAGATC CAGTACAGGA AAGACACGGC CACGTGGAAG GACAGCAAGA
1351 CCGAGACCCT CCAGAACGCC CACAGCATGG CCCTGCCAGC CCTGGAGCCC
1401 TCCACCAGGT ACTGGGCCAG GGTGAGGGTC AGGACCTCCC GCACCGGCTA
1451 CAACGGGATC TGGAGCGAGT GGAGTGAGGC GCGCTCCTGG GACACCGAGT
1501 CGGTGCTGCC TATGTGGGTG CTGGCCCTCA TCGTGATCTT CCTCACCATC
1551 GCTGTGCTCC TGGCCCTCCG CTTCTGTGGC ATCTACGGGT ACAGGCTGCG
1601 CAGAAAGTGG GAGGAGAAGA TCCCCAACCC CAGCAAGAGC CACCTGTTCC
1651 AGAACGGGAG CGCAGAGCTT TGGCCCCAG GCAGCATGTC GGCCTTCACT
1701 AGCGGGAGTC CCCCACACCA GGGGCCGTGG GGCAGCCGCT TCCCTGAGCT
1751 GGAGGGGGTG TTCCCTGTAG GATTCGGGGA CAGCGAGGTG TCACCTCTCA
1801 CCATAGAGGA CCCCAAGCAT GTCTGTGATC CACCATCTGG GCCTGACACG
1851 ACTCCAGCTG CCTCAGATCT ACCCACAGAG CAGCCCCCA GCCCCCAGCC
1901 AGGCCCGCCT GCCGCCTCCC ACACACCTGA GCCTTATCAG ACTGAGATGC
1951 GGCTGGTTGT GTTGAGGACT TGTGTGGGCT GCCTGTCCCC GGCAGTCGCT
2001 GATGCACATG ACATGATTCT CATCTGGGTG CAGAGGTGGG AGGCACCAGG
2051 TGGGCACCCG TGGGGGTTAG GGCTTGGAAG AGTGGCACAG GACTGGGCAC
2101 GCTCAGTGAG GCTCAGGGAA TTCAGACTAG CCTCGATTGT CACTCCGAGA
2151 AATGGGCATG GTATTGGGGG TCGGGGGGC GGTGCAAGGG ACGCACATGA
2201 GAGACTGTTT GGGAGCTTCT GGGGAGCCCT GCTAGTTGTC TCAGTGATGT
2251 CTGTGGGACC TCCAGTCCCT TGAGACCCCA CGTCATGTAG AGAAGTTAAC
2301 GGCCCAAGTG GTGGGCAGGC TGGCGGGACC TGGGGAACAT CAGGAGAGGA
2351 GTCCAGAGCC CACGTCTACT GCGGAAAAGT CAGGGGAAAC TGCCAAACAA
2401 AGGAAAATGC CCCAAAGGCA TATATGCTTT AGGGCCTTTG GTCCAAATGG
2451 CCCGGGTGGC CACTCTTCCA GATAGACCAG GCAACTCTCC CTCCCACCGG
2501 CCACAGATGA GGGGCTGCTG ATCTATGCCT GGGCCTGCAC CAGGGATTAT
2551 GGTTCTTTTA AATCTTTGCC TTTCAGATAC AGGAAAAATA ATGGCATTAA
2601 ATTGCTTTAA TTTGCATTAT TTTAGTTATC CAGTTTGCAC ATATTTTTAT
2651 AGGTATCTTA GGCATCGATT GGTATTTTTT AACTGGGCCA AGCCCATTAA
2701 GGTCTTTCTT CTGTTGGGTG CTATCATTTT CTGATTAAGT CTTTTTGACT
2751 ATTGACATAC AGTCTTTCAC AGATGGTGGA GTGTTTTTCC CCCAAATCTG
2801 TTGTTTGTCT TATAATGTTG TATATGAGGT TTTATGGTGT ATGAATATGA
2851 ATGCTTCTGT AATGTCAAAC AGATCCCTAG TAAACTCCTT CTTCACTTTT
2901 ACTGTCAGAT TTACAAAGGT CCTCCCATTG CAAAGCAGTG TTTGTCCTAA
2951 TTCATATATC GTTTTTCTAG TCCATTTTGT GTTTCCAACC CTTTATGTAA
3001 AATCTTAATT ATTTCTTGAA TGTGTGGATG TGAAACTGAG GCGGCCTTTC
3051 CGGAACTGAA ATACTTATAA GACATGACCC GTGTGAGTGA CACTTTTTGC
3101 GGATTCATGA ACACTCCTCC CGTTCATCTC CGTTCCCCGC CCCCCCATGC
3151 GTTAATTTTC TTTTTATTTT TAGACGTTGA CGGCAGCCAG CTTACCCGCC
3201 GTCTTTTATC TTGGTCCCCA CCTCGAGTTC CGCCCCGCAT AGTGTTAACC
3251 GGACGCGCCC TCCAGCCGTC CCTGGACCGT ATCCATGTAC TTGTATTCCT
3301 ACACCGCCCC TTCTGCCGCC ACCACAATAA AGTGGCTACA AATGTATTGC
3351 ATGCGAGCGC ACCCTTTTAC CCCCCTCTGC CTGACGCGCC CCCC (SEQ ID NO:1)
```

FIGURE 1A

```
FEATURES:
5'UTR:          1-188
Start Codon:    189
Stop Codon:     2271
3'UTR:          2274
```

Homologous proteins:
Top 10 BLAST Hits

```
                                                                      Score      E
CRA|18000004922346  /altid=gi|4559408  /def=ref|NP_000386.1| colo...   1233    0.0
CRA|18000004948483  /altid=gi|106168   /def=pir||A39255 cytokine r...  1231    0.0
CRA|18000005149407  /altid=gi|3169005  /def=emb|CAA15487.1| (AL00...    927    0.0
CRA|18000005185853  /altid=gi|3882358  /def=gb|AAC77520.1| (U9468...    766    0.0
CRA|18000004935123  /altid=gi|6681049  /def=ref|NP_031807.1| colo...    677    0.0
CRA|18000004994803  /altid=gi|110596   /def=pir||A40091 interleuki...   677    0.0
CRA|18000004933239  /altid=gi|6681047  /def=ref|NP_031806.1| colo...    670    0.0
CRA|18000005011206  /altid=gi|2118669  /def=pir||I56563 interleuk...    664    0.0
CRA|114000015335379 /altid=gi|9488658  /def=gb|AAB31055.2| (S703...     448    e-124
CRA|114000015331865 /altid=gi|9257034  /def=pdb|1C8P|A Chain A, ...     219    2e-55
```

BLAST dbEST hits:

```
                                              Score      E
gi|12401717  /dataset=dbest /taxon=96...       831    0.0
gi|12396693  /dataset=dbest /taxon=96...       831    0.0
gi|12440910  /dataset=dbest /taxon=96...       831    0.0
gi|12394121  /dataset=dbest /taxon=96...       714    0.0
gi|12870508  /dataset=dbest /taxon=960...      466    e-128
gi|12291346  /dataset=dbest /taxon=96...       394    e-107
gi|1275610   /dataset=dbest /taxon=9606 ...    333    1e-88
gi|12392610  /dataset=dbest /taxon=96...       246    2e-62
```

EXPRESSION INFORMATION FOR MODULATORY USE:
library source:
From BLAST dbEST hits:
```
gi|12401717    Placenta normal
gi|12396693    Placenta normal
gi|12440910    Placenta normal
gi|12394121    Placenta normal
gi|12870508    Placenta normal
gi|12291346    marrow
gi|1275610     Liver and spleen
gi|12392610    Placenta normal
```

From PCR-based tissue screening panels:
Human leukocytes

FIGURE 1B

```
  1 MVLAQGLLSM ALLALCWERS LAGAEETIPL QTLRCYNDYT SHITCRWADT
 51 QDAQRLVNVT LIRRVNEDLL EPVSCDLSDD MPWSACPHPR CVPRRCVIPC
101 QSFVVTDVDY FSFQPDRPLG TRLTVTLTQH VQPPEPRDLQ ISTDQDHFLL
151 TWSVALGSPQ SHWLSPGDLE FEVVYKRLQD SWEDAAILLS NTSQATLGPE
201 HLMPSSTYVA RVRTRLAPGS RLSGRPSKWS PEVCWDSQPG DEAQPQNLEC
251 FFDGAAVLSC SWEVRKEVAS SVSFGLFYKP SPDAGEEECS PVLREGLGSL
301 HTRHHCQIPV PDPATHGQYI VSVQPRRAEK HIKSSVNIQM APPSLNVTKD
351 GDSYSLRWET MKMRYEHIDH TFEIQYRKDT ATWKDSKTET LQNAHSMALP
401 ALEPSTRYWA RVRVRTSRTG YNGIWSEWSE ARSWDTESVL PMWVLALIVI
451 FLTIAVLLAL RFCGIYGYRL RRKWEEKIPN PSKSHLFQNG SAELWPPGSM
501 SAFTSGSPPH QGPWGSRFPE LEGVFPVGFG DSEVSPLTIE DPKHVCDPPS
551 GPDTTPAASD LPTEQPPSPQ PGPPAASHTP EPYQTEMRLV VLRTCVGCLS
601 PAVADAHDMI LIWVQRWEAP GGHPWGLGLG RVAQDWARSV RLREFRLASI
651 VTPRNGHGIG GRGGGARDAH ERLFGSFWGA LLVVSVMSVG PPVP    (SEQ ID NO:2)

FEATURES:
Functional domains and key regions:
Prosite results:
PDOC00001 PS00001 ASN_GLYCOSYLATION
N-glycosylation site
Number of matches: 4
        1    58-61        NVTL
        2    191-194      NTSQ
        3    346-349      NVTK
        4    489-492      NGSA PDOC00004 PS00004 CAMP_PHOSPHO_SITE
cAMP- and cGMP-dependent protein kinase phosphorylation site
             377-380      RKDT PDOC00005 PS00005 PKC_PHOSPHO_SITE
Protein kinase C phosphorylation site
Number of matches: 10
        1    32-34        TLR
        2    44-46        TCR
        3    223-225      SGR
        4    355-357      SLR
        5    360-362      TMK
        6    382-384      TWK
        7    405-407      STR
        8    416-418      TSR
        9    639-641      SVR
       10    652-654      TPR PDOC00006 PS00006 CK2_PHOSPHO_SITE
Casein kinase II phosphorylation site
Number of matches: 8
        1    106-109      TDVD
        2    143-146      TDQD
        3    165-168      SPGD
        4    181-184      SWED
        5    382-385      TWKD
        6    386-389      SKTE
        7    538-541      TIED
        8    550-553      SGPD
```

FIGURE 2A

```
PDOC00008 PS00008 MYRISTYL
N-myristoylation site
Number of matches: 9
        1       23-28           GAEETI
        2       120-125         GTRLTV
        3       157-162         GSPQSH
        4       219-224         GSRLSG
        5       298-303         GSLHTR
        6       498-503         GSMSAF
        7       626-631         GLGLGR
        8       660-665         GGRGGG
        9       675-680         GSFWGA PDOC01053 PS01355 HEMATOPO_REC_S_F1
Short hematopoietin receptor family 1 signature
            402-434     LEPSTRYWARVRVRTSRTGYNGIWSEWSEARSW
```

Membrane spanning structure and domains:

| Helix | Begin | End | Score | Certainty |
|---|---|---|---|---|
| 1 | 147 | 167 | 0.828 | Putative |
| 2 | 440 | 460 | 2.523 | Certain |
| 3 | 490 | 510 | 0.800 | Putative |
| 4 | 673 | 693 | 1.955 | Certain |

FIGURE 2B

BLAST Alignment to Top Hit:
>CRA|18000004922346 /altid=gi|4559408 /def=ref|NP_000386.1| colony
    stimulating factor 2 receptor, beta, low-affinity
    (granulocyte-macrophage); interleukin 3
    receptor/granulocyte-macrophage colony stimulating factor
    3 receptor, beta (high affinity); Colony-stimulating
    factor-2 receptor, beta, low-affinity [Homo > /org=Homo >
    /dataset=nraa /length=897
        Length = 897

Score = 1233 bits (3156), Expect = 0.0
Identities = 581/581 (100%), Positives = 581/581 (100%)
Frame = +3

```
Query: 189   MVLAQGLLSMALLALCWERSLAGAEETIPLQTLRCYNDYTSHITCRWADTQDAQRLVNVT 368
             MVLAQGLLSMALLALCWERSLAGAEETIPLQTLRCYNDYTSHITCRWADTQDAQRLVNVT
Sbjct: 1     MVLAQGLLSMALLALCWERSLAGAEETIPLQTLRCYNDYTSHITCRWADTQDAQRLVNVT 60

Query: 369   LIRRVNEDLLEPVSCDLSDDMPWSACPHPRCVPRRCVIPCQSFVVTDVDYFSFQPDRPLG 548
             LIRRVNEDLLEPVSCDLSDDMPWSACPHPRCVPRRCVIPCQSFVVTDVDYFSFQPDRPLG
Sbjct: 61    LIRRVNEDLLEPVSCDLSDDMPWSACPHPRCVPRRCVIPCQSFVVTDVDYFSFQPDRPLG 120

Query: 549   TRLTVTLTQHVQPPEPRDLQISTDQDHFLLTWSVALGSPQSHWLSPGDLEFEVVYKRLQD 728
             TRLTVTLTQHVQPPEPRDLQISTDQDHFLLTWSVALGSPQSHWLSPGDLEFEVVYKRLQD
Sbjct: 121   TRLTVTLTQHVQPPEPRDLQISTDQDHFLLTWSVALGSPQSHWLSPGDLEFEVVYKRLQD 180

Query: 729   SWEDAAILLSNTSQATLGPEHLMPSSTYVARVRTRLAPGSRLSGRPSKWSPEVCWDSQPG 908
             SWEDAAILLSNTSQATLGPEHLMPSSTYVARVRTRLAPGSRLSGRPSKWSPEVCWDSQPG
Sbjct: 181   SWEDAAILLSNTSQATLGPEHLMPSSTYVARVRTRLAPGSRLSGRPSKWSPEVCWDSQPG 240

Query: 909   DEAQPQNLECFFDGAAVLSCSWEVRKEVASSVSFGLFYKPSPDAGEEECSPVLREGLGSL 1088
             DEAQPQNLECFFDGAAVLSCSWEVRKEVASSVSFGLFYKPSPDAGEEECSPVLREGLGSL
Sbjct: 241   DEAQPQNLECFFDGAAVLSCSWEVRKEVASSVSFGLFYKPSPDAGEEECSPVLREGLGSL 300

Query: 1089  HTRHHCQIPVPDPATHGQYIVSVQPRRAEKHIKSSVNIQMAPPSLNVTKDGDSYSLRWET 1268
             HTRHHCQIPVPDPATHGQYIVSVQPRRAEKHIKSSVNIQMAPPSLNVTKDGDSYSLRWET
Sbjct: 301   HTRHHCQIPVPDPATHGQYIVSVQPRRAEKHIKSSVNIQMAPPSLNVTKDGDSYSLRWET 360

Query: 1269  MKMRYEHIDHTFEIQYRKDTATWKDSKTETLQNAHSMALPALEPSTRYWARVRVRTSRTG 1448
             MKMRYEHIDHTFEIQYRKDTATWKDSKTETLQNAHSMALPALEPSTRYWARVRVRTSRTG
Sbjct: 361   MKMRYEHIDHTFEIQYRKDTATWKDSKTETLQNAHSMALPALEPSTRYWARVRVRTSRTG 420

Query: 1449  YNGIWSEWSEARSWDTESVLPMWVLALIVIFLTIAVLLALRFCGIYGYRLRRKWEEKIPN 1628
             YNGIWSEWSEARSWDTESVLPMWVLALIVIFLTIAVLLALRFCGIYGYRLRRKWEEKIPN
Sbjct: 421   YNGIWSEWSEARSWDTESVLPMWVLALIVIFLTIAVLLALRFCGIYGYRLRRKWEEKIPN 480

Query: 1629  PSKSHLFQNGSAELWPPGSMSAFTSGSPPHQGPWGSRFPELEGVFPVGFGDSEVSPLTIE 1808
             PSKSHLFQNGSAELWPPGSMSAFTSGSPPHQGPWGSRFPELEGVFPVGFGDSEVSPLTIE
Sbjct: 481   PSKSHLFQNGSAELWPPGSMSAFTSGSPPHQGPWGSRFPELEGVFPVGFGDSEVSPLTIE 540

Query: 1809  DPKHVCDPPSGPDTTPAASDLPTEQPPSPQPGPPAASHTPE 1931
             DPKHVCDPPSGPDTTPAASDLPTEQPPSPQPGPPAASHTPE
Sbjct: 541   DPKHVCDPPSGPDTTPAASDLPTEQPPSPQPGPPAASHTPE 581   (SEQ ID NO:4)
```

Hmmer search results (Pfam):

| Model | Description | Score | E-value | N |
|---|---|---|---|---|
| PF00041 | Fibronectin type III domain | 27.4 | 1.8e-06 | 2 |

Parsed for domains:

| Model | Domain | seq-f | seq-t | hmm-f | hmm-t | | score | E-value |
|---|---|---|---|---|---|---|---|---|
| PF00041 | 1/2 | 133 | 227 .. | 1 | 84 | [] | 18.4 | 0.00073 |
| PF00041 | 2/2 | 341 | 426 .. | 3 | 84 | .] | 10.4 | 0.15 |

FIGURE 2C

```
   1 TGACTGTCGA CCAATTACAT AACATCCCAC CCCTGTTTTC TCATCTACAA
  51 AGTGGAGCTT CTAGTGGTAA CCTATACATA GATGTATTCA TATCCGTAAA
 101 ACCTTTTGAA TAATGCCTGG CTCATGGAAA ACACTGCAAT ATTGTCAGCC
 151 ACTATCATGA ATTCTCTCTG TGTATGTGAG TACTGTTTGT GCTCTTTGAT
 201 GATATTGATT TGTTTTAACC TTTTAAAGTA AAAGACACTA ACCTGTCCTC
 251 CATAATTCTG GTTGGTATGG TCTATATGTT GAAGTGCACC CAAGTTTATG
 301 TTGCAACCTA AGCCCCAATG TGAGAATATC TGGAGGTAGT GCCTGTGGCA
 351 CCCTATAAAA TACCCCAGCG AGCTCCCTTG CTTATTCCAT GTGAGATTAC
 401 AGGGAGAAGA CTGCAAGGAA CAGGCCCTCA CCAGATAGTG AATCTGCCCG
 451 CACCTTGATC TTGAACTTCC CAGCCTCCAG AACTATGAGA AATAAACTTT
 501 GTTACTAGTA AGCCACTCCA TCTATGGTAT GTTGTTACAG TAGCCTAACG
 551 GATGAGTACA TTGGTGCAAA GATTTTCTGT TTGCACTCCG TCCTTTCCTT
 601 TTATGGTTCA GTCAGTTTGA CAAATTACAG AAGATTTCAC TTTTATGTAC
 651 TTCTGCCAGC CTTTGTCTCT GTGATGTCTC CTATGCTTTT AAGCTTAAAG
 701 AGTTCAAAGG CATTCACTCC TCTGGTTTGC AGCTTTCATA GGATGTAACA
 751 TTTTACATTT AAATTTATAA TTAACTTGTT ATTTGGGGAA TGGTGTGAAA
 801 TGGGGTTTTA GATAGGCATT TTTATGTTGT TAATCAATGA TTTTAGCATT
 851 TTTTTAAATT TAATATTTCA TCGCTTCACA TTGATTCCTG ATTCCTTCTC
 901 AGTCTGGGGT CAAGTAGAGT TTGTTTCCAG CCAGCATGTC CATTGATAGA
 951 TTCTGTGTGT GTGTATGTGT GTCTGTGCAT GTATCTGTAT GTGTGTGTGT
1001 ATGTCTGTGT GTAGGTGGTA TATGCGAGTG TGTATGTGTG TGTGTGTTGT
1051 GCATGTATGT GTATGTGTGT CTGTGTATGT GTGCCTCTGT GTGTGAATTT
1101 CTGTGTATGT GTGAATGTGT GTGCATGTTT GTGTGTATAT GTGTATATAT
1151 GTGTATATAC ATGTATGTAT CTGTGTTGTT CATGTGTGTA TGTGTGCCTG
1201 TGTCTCTGTG TGTGTGTTTG TATGTGTGTG TGCATGTTTG TGTGTGTATA
1251 TGTGTGTATA TTGTATGTAT CTGTGTGTGT CTGTGTCTGC CTCTGTGTGT
1301 GTGTCTGTGT GTGCATTTGT GTGTATACAT GTGGGTATGT GTGTGCATGT
1351 TTTGTGTGTA CGTGTATATA TGTATGTATC TGTGTGTGT TGTGTGTTGT
1401 GCGTGTGTGT GCCTGCATGT GTCCGTGTGC TTGTGTGTGT GTGTGTGTTT
1451 GCGTGGGCAT CTTGAGTGAA GCTTCCAACA ATCTAACAGA AGAAAAGGAG
1501 CCACACTTGT CTGTTCTGCT CTCTTGGGTA CTTCCCAGAC CAGTGAAATG
1551 AAAGGGAGGA AACCCCCGGC CTCCGAGGAG AAAAGGGAAC TGGCAAGCAG
1601 AGGGTGGGGG GATGACGGTA AAAGGAGCAG GGGTGGGGAG AGCACAGGCC
1651 CTGTGGAAGT GAGGACATGT GTGTGTACAT GTGTTCATGT CCAGGGGATG
1701 ACACTGTGGC ATCCAACAGC CGTGGACCAG CAGCCCACGG GGAGCTTAGT
1751 AGGAGTCAAA TCCTAGGCCC CCGTCTCAGC TGCTCTGCTG TCTAGCGCAT
1801 TGTGCAGTGG TAGGTGTCAG TGATCCAAGT GGGGACCCAG TCCCTCAGGC
1851 CACACAGCGC ATGTCCATTG CCTTCATGCC GCAGGAGACT GAGGGGTCAT
1901 GCATGAGGGC CACTTCTCTG GGTTGTCCCC ACAACACTGG CGGTGTCCCT
1951 GGGACATGTG GAAAGGGGAG GGGCAGCTCA CTGCTGACAT CTCCTTCTGC
2001 AGGCCTGGAG GAGGCAGAGG CCAGGAGGGA GAGGTCCCAA GAGCCTGTGA
2051 AATGGCTCTG GCCTGGCTCC CAGGTGACCA GGAACACAGG ACTTCAGGAC
2101 ACTAAGGACC CTGTCATGCC CATGGCCAGC ACCCACCAGT GCTGGTGCCT
2151 GCCTGTCCAG AGCTGACCAG GGTAGATGGT GCTGGCCCAG GGGCTGCTCT
2201 CCATGGCCCT GCTGGCCCTG TGCTGGGAGC GCAGCCTGGC AGGGGCAGAA
2251 GGTGAGTCCC GTGGCTCCCA CCCACTTCCC TGTCCCTGTC CTCACTGCTG
2301 CACCCTGGGG GAGGGCCGCA GCGTATCCTC AGGATCCTGC CCGCCAGCCC
2351 TCCTCCTGCT CCCCTCCCTC TGTCTCTCCC CCTGGCCTTC CCTGGGCCTC
2401 CCCCGCCTTC CTCCTCCTGC ACATTCCTGC TCATCCTGTC TTGGAAAGTC
2451 CAGCTGAGCG TGTCTGGCTT CCTTGCCCAC ATTTCTCAGG GCGGCACTCC
2501 CGGCCCCTAG GCTCCAGGAT GGCTGCTCTG GCCGTTTCCC TGCCCCTCCT
2551 TCCCCAGCAG ACACTCTCTG TGCCTCAGTG GTTCCCACCT CCGGGACTTT
2601 GCTCCTGCAG GGCCTTGGCT GGGGTTCTCT CCCTGCTTCA GCCGCTAGCA
2651 CCCTCCTTGT GCCTGAAGCC CGCACTGGGA TGCTCCTGGG CTCTTGAGGT
2701 GAAATGGCCC CTCCCAAGGG CTCCCAGAGA CCTGGCTTCT GTGATAATGC
2751 TGGGACCACA GTCCCCTTAA CAAATACCAG GCTCCTCACG ACGGGGACTA
2801 GAGAGGAGGT GGGAGGTTGC AGGGTAGAAC TCTGCCACGC TGCATCCCAG
2851 GGCTGAGTGT GTGCCCCCTC CCAGGCTGCA CAGTCGGTCC AGGGGCCAGG
2901 CCTGTGCTTG ATGCATGTCC CTGTCCTGGG GTGGGGGGAG GGGACCGTGC
2951 CCAGGAACAG CACACTGCGG AGGCCCAGAA ACCATGCTGA GAACCAACAG
3001 AATGTCTTGC TTCTGCCAGG AGAGGAGGGT CCGCAACCAG GAGCCCACCC
3051 CGGCAGACAT GAACACATGT ACATGTGCCT GGCCACCTGG TGCCTCTGCA
3101 GGGACCTGGG AGACCCCTCC CCAGAGCGGG ACATCCCAAA GCAGCTGGGG
3151 GTGATGGTGA CAAGGGTCCC TGCAGGAAAG AGAGGTGACC CCCTTCTACC
3201 CCTCTTGTCA GAAACCATCC CGCTGCAGAC CCTGCGCTGC TACAACGACT
3251 ACACCAGCCA CATCACCTGC AGGTGGGCAG ACACCCAGGA TGCCCAGCGG
3301 CTCGTCAACG TGACCCTCAT TCGCCGGGTG AATGAGTGAG TGATGCTGGG
3351 GCAGGGGCCA CGGGCNNNNN NNNNNNNNNN NNNNNNNNNN NNNNNNNNNN
```

FIGURE 3A

```
3401 NNNNNNNNNN NNNNNNNNNN NNNNNNNNNN NNNNNNNNNN NNNNNNNNNN
3451 NNNNNNNNNN NNNNNNNNNN NNNNNNNNNN NNNNNNNNNN NNNNNNNNNN
3501 NNNNNNNNNN NNNNNNNNNN NNNNNNNNNN NNNNNNNNNN NNNNNNNNNN
3551 NNNNNNNNNN NNNNNNNNNN NNNNNNNNNN NNNNNNNNNN NNNNNNNNNN
3601 NNNNNNNNNN NNNNNNNNNN NNNNNNNNNN NNNNNNNNNN NNNNNNNNNN
3651 NNNNNNNNNN NNNNNNNNNN NNNNNNNNNN NNNNNNNNNN NNNNNNNNNN
3701 NNNNNNNNNN NNNNNNNNNN NNNNNNNNNN NNNNNNNNNN NNNNNNNNNN
3751 NNNNNNNNNN NNNNNNNNNN NNNNNNNNNN NNNNNNNNNN NNNNNNNNNN
3801 NNNNNNNNNN NNNNNNNNNN NNNNNNNNNN NNNNNNNNNN NNNNNNNNNN
3851 NNNNNNNNNN NNNNNNNNNN NNNNNNNNNN NNNNNNNNNN NNNNNNNNNN
3901 NNNNNNNNNN NNNNNNNNNN NNNNNNNNNN NNNNNNNNNN NNNNNNNNNN
3951 NNNNNNNNNN NNNNNNNNNN NNNNNNNNNN NNNNNNNNNN NNNNNNNNNN
4001 NNNNNNNNNN NNNNNNNNNN NNNNNNNNNN NNNNNNNNNN NNNNNNNNNN
4051 NNNNNNNNNN NNNNNNNNNN NNNNNNNNNN NNNNNNNNNN NNNNNNNNNN
4101 NNNNNNNNNN NNNNNNNNNN NNNNNNNNNN NNNNNNNNNN NNNNNNNNNN
4151 NNNNNNNNNN NNNNNNNNNN NNNNNNNNNN NNNNNNNNNN NNNNNNNNNN
4201 NNNNNNNNNN NNNNNNNNNN NNNNNNNNNN NNNCTCCCCA CCCCCTTTGC
4251 CCACCGCCGG GGCCTGGGCC TGGACCAGGG CTCCTGTCTG AGGCCTGAGA
4301 CACGATGCTG TCTGGTCCTG TTGCTCAGGA ACATCACGGC CCCCAAGTCC
4351 CCACTCTGCC CTGTGCCACC CACCATGCCC TCTCCCAGGA TCTTTCCCAA
4401 TTGCCTTGCA AACCTGCCCC AACCCCTCT CAGATGCCCA CAGGAGTGCA
4451 GCGCCTGGGC ATCTCCTGAC CTGGCAACCC TGCGGCCCCT CTTTCTCTGC
4501 TTCCTTTGAC AGCAGCATTC CCTAAAGAGT TGTCCACATT CACCACGTCC
4551 AGTGTCTTTC CAGCCATTTC CTCCTGGGCC CACTCCCCTA GGATGCTGCC
4601 CCCACCAGGC CACCCAAACT GCTCTGGTCC AAGTCAGCAA ATGTCCCAGG
4651 GAGCAGGATC TCATGGTTGG GCCTCCGCCT TCTTCCTACT TGACCAGGGG
4701 CAGCCCCTGA CAAGGAGGAC CACCGCGGCC TCCCTGCAGT TTCTCTTGCA
4751 CCTGACTCTG CCCACAGCTC ACCCAGTGCC CCCGGGGCCC TGCCCATCCT
4801 CTCTTTCTCC TTGTCTGCTG CCTCCTGATG GCAAGACACC CAGGCCCAGT
4851 CCATGGACCT CCTCTCTGCT GTATCCACTC TGCAGAGACC CCCTCAGGCC
4901 CCTGGGGCAT CTCCCAAAGG TGACCTCAAG CCCACAATTC CCCTAAGCTC
4951 CAGCCCTCCA GGCGTACTGG CCTCTCCACC TGTCACTTAG ACAACAGGTG
5001 TCTCCGACTC CAAACGTCCT CAACCAAAGT CCCGCTCTCA CCCGAGCTGC
5051 GCTGCTGCCT CTGTCTTCCC CATCTCCCTT TCTAAATGGG AGCTCCTAGT
5101 GGCTCCAAACT AAACAACAGG GAGGATTTTG TTTTGTTTTT AAGTCTCTTT
5151 TGTCACCATT CCTTCCTGAC TGCTACATCC CTCCACCAGC AAATGCTGCC
5201 AACCTTATCT CAAGCAGAAC ATGAATCTCA CCCACGCCAG CCTGACCACC
5251 CTGTTGCACG CCACTTCCTG TCACCTGAAT ATTCCAGAAG CCTCGTAACT
5301 GGGCTCCCTG CTTCCAACAT TGCCACATTC CCACCTCAGT CTATTCGCAA
5351 CCGAGGACCC TCAGGAATCC TTTCAAAGCA TTTATCAAAA TCTACAACAC
5401 CTCTGCTCAT GACTGTTTCC CACTCACTCG CAGTGAGATC CAATCCCATC
5451 ATGTAGATGG ATGGGTCTCC TAGACCTCCC TATCACACGC TCTACTCCCT
5501 GCGCACTGGT TTTAGGCCAA GCCACGCAGC ACACCAAACT CTGCCTGTCC
5551 CAGGGCCTTT GCACGTGCTG TTCCCATTTC CTGAAATCCT CACAATTTGC
5601 ACAGTCCCTC CCTCAATGCC TTTAACATTC TGCCCCCAGG TCACCTCCTT
5651 AGAGAAGCCT GCTTGTCCCA TATTTCAAAT TGCCTCCCTG GCCCAGCCCT
5701 TCCTGCCTCC TCACCTGCTT CTTGCTTTAT TTTTCCACAT GAAGTTCTCT
5751 CCACTGCACA CGCTACACAC TTTGTTCCAT GCAGGTCCCC TTCTCCCAGG
5801 ATGGCAGCTC CGTGGGCAGG ATTTTTGTGT GTTTTATCAC TGCTGGCCCC
5851 TGATTCTGAA CAGAGCCAGG CATGTGGTGA GCACTCAGGA AACCTTTCGT
5901 GAGTCAGTGA TACCCATACA CCCTGGGCTA AGCCGTGTCC TCTCCCAACA
5951 GGGACCTCCT GGAGCCAGTG TCCTGTGACC TCAGTGATGA CATGCCCTGG
6001 TCAGCCTGCC CCCATCCCCG CTGCGTGCCC AGGAGATGTG TCATTCCCTG
6051 CCAGAGTTTT GTCGTCACTG ACGTTGACTA CTTCTCATTC CAACCAGACA
6101 GGCCTCTGGG CACCCGGCTC ACCGTCACTC TGACCCAGCA TGGTGAGGGG
6151 CTGGGGGCCC TGCCCGGGGC TTGGTTTCCT GTGTGGACAG CGGGGGCACC
6201 AGGGGTGGTC CAGGGAGTCT TCAAGGCAGA AGGCTGTGGC TTGGGGTTGG
6251 GTGAGGGTTT CTTGAGGGAT GAGGGTATGG TCTGGTTACA TGGAGACTTC
6301 AGAGCAGAGG GGCCCCTGAC AAAGGCTTCT CCTGTGCCCC TGGCTGCTAC
6351 CACCTCCCAC TAAGCCATGG GCTTCCAGCA CTGCAGGCTT GTCTTGAAGA
6401 AAACCGTTCT CACCACTCAC TTAGAAACCT ACCAAGTTAG AAAACTCTGT
6451 CCGCTTAGTT GTTTCATCTC ATCTCTGAAG CAACCCATTT CCTGGATGTG
6501 GCCCTTGAGG CCCAGGAGGT CAGATGCCTC CTCTGAAGTC CCACAGCTGA
6551 GCAGTAATGA CAGAGATGGG GTCAGCCTTC CCGGGGGCTT CCTGCATGGT
6601 AGACAGGGAG CTTGTCTCCT CGCTGCCCTG GAGGAGGGGC CCCGGTGTGG
6651 GCCGAAATCC CACAGTGGTC CATGAAGCCA TCTGTGGTCT AGGGTGGGGT
6701 AGATGATTAT TTTATGTAGT TAGGTTTTAT TTGCCTCTAT ATTAGAAAGA
6751 AATATAACCT GCACTTCGAA GTCCTGGATT CAAGGAAATG GTTGCTTAGA
```

FIGURE 3B

```
 6801 ATGAAGCTAA ACCTGAAAAG GGACACGTTT TATGAAAGTT TTCGTTGACG
 6851 TGGCAAAAAC CCATGCTGGT GGCAGGCTGG TAGGAGGTAC TGCAGGCTGT
 6901 CATTGGGAGT CTCAGAACCA CGGCAGGCTT GGTGCTGTTA TTGGTGCCTT
 6951 TGGCTGCTGC TGAAACGGAG ACAGAGGGAG GTGACTAGTC CAAGGCCTCT
 7001 CTACTGCTGC TGGCAGAGCT GAGATCCAGT GCAGGATGGT CTGAGTCCCC
 7051 GGTCCTAACC ACCGAACCAC CTGGTGCTCT TTGCAAGGGT CACACGGAAG
 7101 GGGCTCTGAC CATGGCTTCC TGCCCTTTTT TGCCACAACA TCATAAAGCC
 7151 ACTGCCAGAG GAGGGGATCA GTTAGGCCAC CAGGAGTCCA TCAGAAGCAA
 7201 CATTTCCACA CATGGGTTTG ATGGACACGA GAGTCCCTTC CTTCCCGAAT
 7251 GGAGCTCAGG GGGCCCAGGC TGGAGGGAGG GGAAACACTG TATGCCGTCC
 7301 ACCGTGAGAA CTTACTGACA GTGGCGGGTG GGTGCCTCAT GCAGGGGGTA
 7351 AAGGGCAGGG CCCCTGGGAG ATCAGAACAG GCTTCCCAGA GGGAAGAGCT
 7401 TTGCAACTCA GATCTGAAGG GTAGACAGGA GGGGAGGGCA GTAAGAGCCT
 7451 CTCTGGCAGG GTAACAGCTG TGCAGAGGCT GGGGGATCAG AAGGGCATGG
 7501 GCAGCTGGGG AACCTGCTCA CCATTGTGTC CAGGGAGCAT CAGCTTCAAG
 7551 GGCTGGACAG CGGTGGGAAG AAGCAGGAGA CACAGGTAAG GACCTGTCCC
 7601 TGGAGAGGCT TCTGTCTCCT GCAGTCTCAG GTAGAGGGGA CCCTCTAGGC
 7651 ATGGAGAGCA CTGAGGGGAA ATGACATGAT CAGATGTGGA TGTGAGAATG
 7701 CTGGGGACAG GGGACTTACA GGGTAGATTG GAGGAGCATT AGTTGGGAAA
 7751 GAAGTTGAAA TTCAGGCTGT GGCCTAAAGC ACTCATTCCT AGAAATGATG
 7801 AGGACACAAC TGGCTAGGAG ATGGGGACAT GAGGGCATGC AAATCATAGT
 7851 TCAGATATAC ACACAATTCA TTCATTCAAC CTTCTTTTCT TGAGCGCCTA
 7901 CATAAGCCAA CGAAGCAGTC AACAAACCAG CCAGCAACCC TGCCCTTGGA
 7951 GCTTACAGCC TGGAAACAAG GAAGGTTTCT AAGGCGATGG AGACAACTTA
 8001 GATATAGGGA GAGAAGTGTG GCCCTTGGCC TCCTGGAGCC TGTGTTGAGT
 8051 AGCGAGGTAG GGTCCAGCCT AATGCAGATT AGCAATGAAT CAAGGATGCT
 8101 GGGAGGTACT GGGCAGGCGA CAGGCATGCA TCTGATCTGC TCTGAGTCTC
 8151 CATGTTTGGA GACCTTGGAC ATTTTACTTC CTCTATGAGT TTCTCCGTCT
 8201 GTGAAATGAG CTGGTGGACT CAAGAGGTTT CTCTTGAGTT GGCTGAGCAG
 8251 GTTTCTGATG GGGCTCCCAG TCTGCGCAGT TTGTGGCAGC TTCCGAGAGG
 8301 GCTCTGCCGG GAAGAGCTCC CCCTCCATGA CAGCCTCGGG GGCTGGGAGT
 8351 GCAGTGACCC ATGAGGGACG CCTGTCCTGG CTGTGGGTGA GGAGGGGCGG
 8401 TTCCCCTGCT GTGTGTCTGC CGTTCTGGGT TGATGGTTCC TGACATGCTC
 8451 TAGCATGCCA TAACCCATGT CCAGCAGAGA GCACTTACAT CCTATGTGTG
 8501 AGGATGTTTT CGTTTGAAAG CCATCCCTCA GCAAGCAGAC ACCAGAAACC
 8551 AGAAATCAGG TGCCGTGTCT TCATTCTGCA TTTTCTTGAA CAACCCAGAG
 8601 TTCCCAGGAG ATAGATGCTT GCCTTGTGGC TGCAAGGATT TCATGAGAAG
 8651 CCCCAAAGTT GCTTACGCGT ATTTGTTCAT TCATTCACTC ATTCACCTTG
 8701 CCCCATAATT CACTGAGAAG CCGCATCTCA GCCTGGAGGT AGGGAAGGGG
 8751 GTCAGGACCA ATCCCACCCA CCCCCATCTC CTCACACCTT AGGGGAGGCA
 8801 GACACAGAAG CATAGGAATC CCTCAGCTGT GGTAAGGCCC TGGTGGAGGG
 8851 AATTCCACTG AGCTATGGTG AAATGAGAGA AGGAATGAGG GATTCCGCCT
 8901 GGAGATGCAG ATCCGAGGAT GTTCCTAGAG CCGGAGGCAT TTGCCCGGGG
 8951 CACTGACAAC AGGAAGGACC CTGGGCAGGA GGAAGGGAGC TTGGACAGCA
 9001 GGAGGGGGGA GGCCGCTGAA CCGCAGGCCC CTCTGCTAGC AGGAGCCACC
 9051 CAGGCCGCAG CGTGGGCAGT GGGGAGCCTC AGGACAGAGG AGGCTCCAAT
 9101 GAGTTTCCTC GCCAGCGCTT TTTATGGAGT TCGGGTCACG TGCGCATTGC
 9151 AATCTGCACG GCTTTCCATT GCTTTCATGT TGAAACCCTA CAGTTTTGCA
 9201 GATGAAGGGC TGAGGCTCAC AGAGGAGACG GGTCTTGCTG AAGGTCCCTC
 9251 AGCTGCTGGG GGCAGGGGTG GCCTGGAACC CCCTGTGTCC ACACAAAAGG
 9301 CCATGCAGGC CCTGACTGCC CCCCAGCGGT CCAGCCCTTA GGTGCCCTTC
 9351 ACTTCCTCCC CTCCAGTCCA GCCTCCTGAG CCCAGGGACC TGCAGATCAG
 9401 CACCGACCAG GACCACTTCC TGCTGACCTG GAGTGTGGCC CTTGGGAGTC
 9451 CCCAGAGCCA CTGGTTGTCC CCAGGGGATC TGGAGTTTGA GGTGGTCTAC
 9501 AAGCGGCTTC AGGACTCTTG GGAGGTAGGA ACCACGGCCA GCTCTGCCCC
 9551 AGCCCGAAGG GATGGGCAGC ACCCCTCCTC CAGCACCCAC TGTCTCCTGA
 9601 CAGGACGCAG CCATCCTCCT CTCCAACACC TCCCAGGCCA CCCTGGGGCC
 9651 AGAGCACCTC ATGCCCAGCA GCACCTACGT GGCCCGAGTA CGGACCCGCC
 9701 TGGCCCCAGG TTCTCGGCTC TCAGGACGTC CCAGCAAGTG GAGCCCAGAG
 9751 GTTTGCTGGG ACTCCCAGCC AGGTAATGTT GCCAGAGCCC AGGAAATGCC
 9801 CCGTGGTGGG AGGGCAGGCT CATCAGGAGC TCCTGGCACA GCAGGGTTCC
 9851 TGGGCTCCAC CTGGGGGCTT CCCAGATCTC CTGCTGCCAT CTTTTCCAGTA
 9901 GCGTCCCTGG GCCGTCCCAC CTCTACTGTG ACCACTGACC AGTAGGACTC
 9951 TGCATCTGTT CACTTTGGGT TTCCAGTTTT CTGCACGTTC TCTGCCAATG
10001 GCAATTACAA TAATAACAAC AACAGTGCTA TTAGCAGCTG TGTGTTAATG
10051 GAGGCTACAG GATGCTCAGG GCTTACCCAC ATTTTTCAGT TCAATCCCCA
10101 AACACTGAAA CTTAGATACT ATTTCCATTC TCCCGGGAGG GCGTGCAGGT
10151 GCACAGAACT CTCTCTCTCT CTCTCGGAGC TGTTGGACAC ACAGCTGGCA
```

FIGURE 3C

```
10201 GGTTCAGGCT GAAGTTTCAG CCCTGGTCTT TTGGCCCCAG AGCTCATGAC
10251 CTCTGTGTGA TGAATCACAC GGTGGGCACC CACTGAGAGC TATGGGAGGG
10301 ATGAATGACG GAGTACATGA GGACCTGTCT CCAACCCAGG GGATGAGGCC
10351 CAGCCCCAGA ACCTGGAGTG CTTCTTTGAC GGGGCCGCCG TGCTCAGCTG
10401 CTCCTGGGAG GTGAGGAGG AGGTGGCCAG CTCGGTCTCC TTTGGCCTAT
10451 TCTACAAGCC CAGCCCAGAT GCAGGGTGAG CATCTTTTTT CTCCATCCCC
10501 TCCCCTCCTC TTGGCCTTGC TCTCTCCAAG CTTCCTCCTG TCCCTGGGGC
10551 CCCAGCAGAA GCCACAGCCC ACCCTAAGCT CTCCTCCCTC CCGTGTGCCC
10601 TCCCTCTCCC TGCCCTCAGC TCTGCTGTGC TCCTCAGGGA GGAAGAGTGC
10651 TCCCCAGTGC TGAGGGAGGG GCTCGGCAGC CTCCACACCA GGCACCACTG
10701 CCAGATTCCC GTGCCCGACC CCGCGACCCA CGGCCAATAC ATCGTCTCTG
10751 TTCAGCCAAG GAGGGCAGAG AAACACATAA AGAGCTCAGT GAACAGTGAG
10801 TTTGCTCCTA GCCCGCTGTG GGGATGGTCT GGGACCAGCA CACCCTCATT
10851 GTGTAACCCG AATCAGTTCA GGGTTCCTCC TGGCCCCGTC TTCATGTTTG
10901 TCACTTTCAA AGAGATGCAG TCCAGTGACC AAAAGTGAAC AGAGAAGCAA
10951 TGAAACCACG ACGGCAGTGG CCAAAAACAG GAGCAGATCT TTAAAACCTC
11001 TGATCTCTTG TCCTTTTCTT CTGCTTCCCT CTCCCATCCT GCAGCTCTCT
11051 AAATCTCCAC TGCTAGCCAC ACCCTCCTGG TCCTGTCACC AAAACCTTCC
11101 CTTTCATTCC TCATTGGATT TTCCTCTTTC TGATATCCGA AATTCCCCAC
11151 CGACTGATAT TCTATCTTTA ATGTAATTGA TCTATGATGT ACTTTTCAAC
11201 TGGAGCCTGT GGTGTGTAAA AATAGTGTTG ATCCTTGGAG GTTAACATCC
11251 CTCGTTTCTG TGATGTAACA AGGACCCCAG TGCAATGGAA CCTCTCACGT
11301 TGTTTCATGA TGACCAAGTT CTTCCATCCA GTCTTTAGCA TATGTGAAGG
11351 GCAGAGGCCA ATTTGTCTTA ATTACCTGGG TTTGAATTTA CCATTAACTC
11401 TCTTGGGATC CTCACTGGAA AAAGGAATTC TGATTGTTCA AAAGCACAGG
11451 ATATATTAAG GGCCTCATAT AATGCCTGGC ACATAAGAGA CCTCAGCAAA
11501 TTACGGGCAT TCATATTATG TTTATACAGT GAAGGCATCA AGGTTATAAG
11551 CATTCTCTTT TTTCTTTTGG GTAGACTGAA GCTCAGAGAG GTTGAGTGGC
11601 TTACTTAAAG CTGCACAGAT ATTAGTAGGC AGATCAAGAT TAGAGTTCAG
11651 AACTTCTCAC TCCCTGCCCA GTTTCTGCTT TCTTTACCCT TTGCCTCTTT
11701 CAAGTTGTGG GTCTGCCGGC CAGGTGGGAG GTGCTGTCTG CAAAGGGCTT
11751 CCCTTTCTCT TTGGCCACTA TCTGGCTGGG GAGAGGCCTC ACCTAGATGT
11801 TGTTGAAGGC CTGTTACAGC CGCTTTATTG GGGATTTTCT GGCGATGAGA
11851 ACGTGTGAAT GTCCTGGCCT TTAGTCAACT CCCTACACCT CTGAGAGTGT
11901 CAGACAAGAG AGCCCATCAC ACTGGTGGGA TTGCAATCTT TGCCTCTACC
11951 ACTGCTTAGC TGCCTTTCCT TAGGGCAAGT TACTTAATGG TTCTGTGACT
12001 CAGTTTCCCT GTTTGTGAAA AGTGAAGGTT AATAGTACCC ACCATATAGG
12051 GCTGTTAGAA TGGAGTGGAA TAATTCATGT AGAATAAGTA TGTATAACAG
12101 TGGCTAAAAC ATAGTCAGGC TGGGCGCGGT GGCTCACGCC TGTAATCCCA
12151 GCACTTTGGG AGGCCAAGGC ATGTGGATCA CGTGAGGTCA GGAGCTCAAG
12201 ACCAGCCTGG CCAACATGGT GAAACCCCGT CTCCACTGAA AATACAAAAA
12251 TTAGCTGGGC TTGGTGGCGG GTGCCTGTAA TCCCAGCTAC TCGGGAGGCT
12301 GAGGCAGGAG AATCACTTGA ACCCAGGAGG CAGAGGTTGC AGTTAGCCAA
12351 GATCACACCA CTGCACTCCA GCCTGGGCAA CAGAGTGAGA CTCCGTCTCA
12401 AAAAAAAAAA AAAAAAAAAT AGCCAGTTGC CTAGAATAGA ACCAACTAAC
12451 AGTGGTTTTA TTTTTACTGC AAAAAATAAA AATAAAAATA GGAGTAGTGC
12501 AAGCACTGGG CCACATCACT ACAAAACAAG TGTATCTCAG CATCTCCCAC
12551 GAGAATACCA CTCAGGTCAA AACATGATAT AGTGAAGTGG GGATGAAAAG
12601 GATCCAACCA TGGGCAGAAC CTGGGGTCTG GTGCCAGTGG AGACAGCCCC
12651 AGTGTCTAGC ATGAGACACG GGGAATGTTC CGTTGGAGGG TGGGTATGAT
12701 GACTCTCCTG AAAGCTTCCC TCCCTCCAGT CCAGATGGCC CCTCCATCCC
12751 TCAACGTGAC CAAGGATGGA GACAGCTACA GCCTGCGCTG GGAAACAATG
12801 AAAATGCGAT ACGAACACAT AGACCACACA TTTGAGATCC AGTACAGGAA
12851 AGACACGGCC ACGTGGAAGG TGAGGGCCTT TGCCCAGGGA CGGGAGAAAC
12901 ACTGGGGAGG GCGGGAGAAG GGAAAGCAAC CAGAGGCATT CCACCTGCAA
12951 GGCGTCGGGC CCTTGGCAGG TGACCAGTGA GAGGTAGCCA CTGGGACGTG
13001 GTGATCACTA GGCTGTGTGG TCAGCAGGTC ACTGTCCTGT CTCTTGGTGA
13051 AGTAACTGAG GTTTGGAAAA GTGGCGTGGC TTGGCCAACG TGAACAGCTG
13101 ACCCTGAGTC CCCAGGCAAC AGAAGACCCT CTGGGCAGGG AGGGGTTGAA
13151 AGGCCACTGG GAAGAAGGTT TTCAAAAGTC ATGAAAGTTT GGGGTTATTT
13201 CCTCAGAGGA ATCTCATCTG GACACACTCA AGGCTCAGA CAGAGCTGCT
13251 TCTAATGAGT CGGGGGTGCG CCCAGGCCAG GGCTCGGTCC CCTGCCTCCA
13301 CAGAGCCCAG AACAGAAACC ACAGAACCAA CCCCACACCT TCAGTCTAGA
13351 AATGGGGCAA CTGAGGCTAG GAGGGAGGTG GGCCAGTGGT GGAGCCAGGA
13401 GCGGGCCCTG GGTCCTGAA CCCCCATTCT CAGGGTCCAG AGTCCAGTCG
13451 GCCTGCACTG CGTTCCTGAA AAGGCACAA TATGGGTGCA AGCTGCCCCA
13501 GAAGGGCTGG GAGCTGAGAA GGCTCAAAAT AGGGTGGGAC AGGTGGCTTC
13551 AGGGTTCTGG GCCTCAGTGT TGTCAATGTC AGGGGCTGCA CTGACAGGCG
```

FIGURE 3D

```
13601 GAGTCCCCGG TGCCATCCGA AGTGCTGTCC GTGGGTGGGC CCTCAGGGAG
13651 GATCCACGGT GGTGAGAGAG AAGCCGCAGC AGGCCTGGGG TATGGCAGGA
13701 GCTAGGAGCC AGCGAAGCCG AGGGTCCAGG TGGGAGGGAT TTGCAGCTGC
13751 TCCCACGGGC ACCGGGCCAG GCCTCACCCT CAGTGCCAAC CCACAGGACA
13801 GCAAGACCGA GACCCTCCAG AACGCCCACA GCATGGCCCT GCCAGCCCTG
13851 GAGCCCTCCA CCAGGTACTG GGCCAGGGTG AGGGTCAGGA CCTCCCGCAC
13901 CGGCTACAAC GGGATCTGGA GTGAGTGGAG TGAGGCGCGC TCCTGGGACA
13951 CCGAGTCGGG TAGGTGAAGG CTGGAGTCCA GAGCTTCTGG CCAGGACCAG
14001 CTCATAGTTT CTCACTGCCA GAAAATCCCC AATGCAGCAG CCGTAGCAGG
14051 CCTGCAACAA CTTGTAGGTG AGCCGTCTCC CCGATTAGAT GGTGGCCAAA
14101 GAGAAAGGGA AGGCCTTTGC AGAGAGCACC TCCCACCTGG TCATCAGACC
14151 CGCAAGTTGA AAGAGGCAAA GGGTAAAGCA GGCAGAAACT GGGCGTGGAG
14201 TCAGAAGTTC TCCACCCACT CTTCATGAGA CAGCACAGCT GGGCAGAGGA
14251 TGCCACATCT CTGGGTGGGC ACAGAGATGT GGGGCTCCAG ACCCCACTCC
14301 ACTCAGGCCT CCTTCCCTCC CTTGGACCAC TAGTCGTTGG AAAGTGACAC
14351 CTGGTGTTCA GTACAGACTG CAAGTGAGGA CTTGAGGGAG CAGAGGAGAG
14401 CAGGTCTCAT GATCGCTCCT CCTTTAAACT GGGACTTAGG CTTCTGTTAA
14451 TATGGCCCTT GGTTTCTTAG CTTTTGGGAC TACCAAGTTT TTGTGGTTGC
14501 TCAGCCCGAG TTTCCTGTTA CCATGGAAGC AAGAAAATCT AGAGCCACAG
14551 ACTGGGTCCT TGGATTGGAA GGTTTTGCTG TGATTCCTTC ATCTTCCCAC
14601 CTCCCTGCAC TTGCTGCGTG CACTGACCCC TCACCTTTCA CCATAGTGAC
14651 CACCAGGCGA CTCCCGCAGA ACAAGACAAG TCCAAGGGGT GGTTTCAGAG
14701 AGAGTAAGGA TACAGGAGAT ATTGGGAGCA ACCCAAGTCC CCAGCCAGGC
14751 TTGGTAGCGG CAGGGGCCCA GGGAGAGGGC CACAACCAGG TAGAAAGGAG
14801 GCCGGACCAA TGGGCCCAAG AGAGGAGGAA GAGGGGAGTC CTGGAGGAAC
14851 CTGGCCTGGG AGCTCAGGGC TGGGCAGCAG GTGGGATCAG GGGCCTCTGG
14901 AGGGGCCTTT GCTCCTGCTG GTGCCTCTGC CACTATGCCT TTCCCCATCT
14951 CCACCTCTAA TCCTTCCTAT TACTGGAGGC CCAGCTAATA TGCCACCTCC
15001 TTCAGGAAGT CCCCTGTGAT TGCCATGAAC AGTGGTTCTT GCCCTCCCTG
15051 TAGCACCTCC TGTGCTATAG ATCCTGGAAA GGATCTGACC CTCCTGTGTC
15101 CTCCCAGCAC TTTGAACACT GTGGGGGTTC AGACCAATGC CCTTCCCAGC
15151 ATGGATCTGG CCTCTCTCCC CTAATCCCCC AAGGCAGTAA GTTCCAGAGC
15201 CCTGGGCCTG CACAGAGCGG GGTCTTAAGG AATACTGCAC CAACCCCACT
15251 CCCTGCCCTG AGGTCGATTT CCCGCCAGA TGCTGACATT CCTCTTTCTC
15301 CCCGGCTGCT GGAAGTGCTG CCTATGTGGG TGCTGGCCCT CATCGTGATC
15351 TTCCTCACCA TCGCTGTGCT CCTGGCCCTC CGCTTCTGTG GCATCTACGG
15401 GTACAGGTGA GGGGACTCTG TGGGCTGGA GGTGGCAGCC GAGACCCCAG
15451 AGGGCACTGG GGAATCCCAC CCAGCTCCCT CCAGGCCCTG CTCTGCCGCT
15501 CCCTTCCTGG GCCTCAGTTT CCCCTCTGGG CATGAGCATG GGAGCAGCTG
15551 GCCATGAGGT CTCTGATGGC TGTCACCTCC CGTGGTGTCT TCCAGGCTGC
15601 GCAGAAAGTG GGAGGAGAAG ATCCCCAACC CCAGCAAGAG CCACCTGTTC
15651 CAGGTAGGAA CTGGCTGCGA GGGGCGGAGT GGGGGCTTCT CTGTTCCTGC
15701 CTCTCTTGTC TCTGTCCCCA CCTCCCTCCT TCCCTTCCTG TGGGCTTTGG
15751 GTGGTAGGGA TGTAGGTGGA CTGGGCTTTG GGAGCTTTGG GAGTGGGGCC
15801 AGCACTTGGA AATTCATTCC CGGGATTCCC TGGAGTGCCC ACACCTGGCC
15851 CTGCCTGCCA GAGCTCTGCA TGGAGCCCAG TGGAGAGAAC TGAGTGTGGG
15901 GATGCCTGGG ACAGGGTGGG CTCACAGAGG GGGTTCCTGC TACCAGGATG
15951 GATGGGGTGT CAGGAGGCAG AAGGGCTCCC CAAGGACAAG ATACCTGGGC
16001 TGAGCTTTGA GGGTCCCAGT GGTGCCAGGT GGCAAAAGTT GCTCTGGCTC
16051 AGGGCATCTT GAGGGTGGAG ACAGAAACCC TTCAGGAAGG GAGCTGAAGG
16101 GGTGGGACAG GAGGCTGGGG GCCATGTTGG GAGGCTGAGA TGACCATGGG
16151 GAAGACACCA GCGTGTGGGT GATGGGAGCC CTATAGTCAG GCAGGCAGGG
16201 CCAGCTTTGC CTGTGGAGGG GTCTCTTGGC TGGTGTGGAG GAGAAATGGG
16251 GGTGAGCATG GAGACAGGCA CTCCAGGTTA GAAAAATCAC AGGAAAAGGG
16301 CCCTGTCCTC AGGTAGCAGG GACATGGGGG AAGTCCCCGC CCCTCTCTGG
16351 GCCTCACTTT GCTGGTGTCA AAAGGCCGTG GCCAGTCCTG AAGAAGTGGA
16401 GATTCTTCTC TTGTCTGGGG GCTCCTTGAA TCCTCCTGCA CCCCCGTCAC
16451 CCTCTGCCTT GCCCCACCT CGGACCTCCT GATGCTCACC GGCCCAAATG
16501 TCTCTGCTCT TGCAGAACGG GAGCGCAGAG CTTTGGCCCC CAGGCAGCAT
16551 GTCGGCCTTC ACTAGCGGGA GTCCCCACA CCAGGGGCCG TGGGGCAGCC
16601 GCTTCCCTGA GCTGGAGGGG TGAGTGGGCT CGTGGATCAC TCCTGACCTT
16651 TGGGGTTCAT ACGGGGGGCT GACTCCATTG TGGAAATCAG GGACTCAAGT
16701 GAGGCTGCCT GTGGCTCACT GTGAAGGGAT CCAAGGGAGC TGGTTTTGCAC
16751 TAAAGCAGGA GGCACCTGGG GGGGATGTGA GGAAGAACTT CCTCTTTCCA
16801 GGTAAGGAAG TGCCAGACAA GGGGAGTGAC CGGAAGTGAA AGAGGGAAAC
16851 AGTTGGCCTT CCCCTCCCTG GCTGCCTCAG AGGCGTCACA CTGCAGAGGC
16901 CTCATGGGGT AGCTGGGGCT GCAGACTCCC GGGAACTCGG CGCCTGAGCC
16951 GGCAGCTGAC CACCAACTCG GCAGGGAGAA GGGGGTGGCA TGGTTGATAG
```

FIGURE 3E

```
17001 AATGATGGAA GGGTTGCCCA GTGCACAGGC TGGGCATGAG CCTGGTGCTG
17051 AAGGAGGATG GACTTTAAGG TCAAAAGGGA GAGGGTACCA GCCTTGCAGA
17101 GGAAGACCTT GAGCTCAGCA TGGAGGATGG AGCTCCTGAG CCACGGAAAG
17151 ACTGAATCCA TGTCCCATGT CCTTCTCTGG GGCCCCTGCT CCCTCAACCC
17201 TGTCCCGTTC AGGTTCTCTC TGTGAGATCT GGGGGACATC AGGGCTTCCA
17251 GAGAACCATC TCCACCCCAC CAAGACCCTT GTGCCTGACC CGGATCATCT
17301 GCCCAGGGTG GTCCCAACTC TTCTGCCCAT TTTCTTCCCA CAGGGTGTTC
17351 CCTGTAGGAT TCGGGGACAG CGAGGTGTCA CCTCTCACCA TAGAGGACCC
17401 CAAGCATGTC TGTGATCCAC CATCTGGGCC TGACACGACT CCAGCTGCCT
17451 CAGATCTACC CACAGAGCAG CCCCCCAGCC CCCAGCCAGG CCCGCCTGCC
17501 GCCTCCCACA CACCTGAGAA ACAGGCTTCC AGCTTTGACT TCAATGGGCC
17551 CTACCTGGGG CCGCCCCACA GCCGCTCCCT ACCTGACATC CTGGGCCAGC
17601 CGGAGCCCCC ACAGGAGGGT GGGAGCCAGA AGTCCCCACC TCCAGGGTCC
17651 CTGGAGTACC TGTGTCTGCC TGCTGGGGGG CAGGTGCAAC TGGTCCCTCT
17701 GGCCCAGGCG ATGGGACCGG GACAGGCCGT GGAAGTGGAG AGAAGGCCGA
17751 GCCAGGGGGC TGCAGGGAGT CCCTCCCTGG AGTCCGGGGG AGGCCCTGCC
17801 CCTCCTGCTC TTGGGCCAAG GGTGGGAGGA CAGGACCAAA AGGACAGCCC
17851 TGTGGCTATA CCCATGAGCT CTGGGGACAC TGAGGACCCT GGAGTGGCCT
17901 CTGGTTATGT CTCCTCTGCA GACCTGGTAT TCACCCCAAA CTCAGGGGCC
17951 TCGTCTGTCT CCCTAGTTCC CTCTCTGGGC CTCCCCTCAG ACCAGACCCC
18001 CAGCTTATGT CCTGGGCTGG CCAGTGGACC CCCTGGAGCC CCAGGCCCTG
18051 TGAAGTCAGG GTTTGAGGGC TATGTGGAGC TCCCTCCAAT TGAGGGCCGG
18101 TCCCCCAGGT CACCAAGGAA CAATCCTGTC CCCCCTGAGG CCAAAAGCCC
18151 TGTCCTGAAC CCAGGGGAAC GCCCGGCAGA TGTGTCCCCA ACATCCCCAC
18201 AGCCCGAGGG CCTCCTTGTC CTGCAGCAAG TGGGCGACTA TTGCTTCCTC
18251 CCCGGCCTGG GGCCCGGCCC TCTCTCGCTC CGGAGTAAAC CTTCTTCCCC
18301 GGGACCCGGT CCTGAGATCA AGAACCTAGA CCAGGCTTTT CAAGTCAAGA
18351 AGCCCCCAGG CCAGGCTGTG CCCCAGGTGC CCGTCATTCA GCTCTTCAAA
18401 GCCCTGAAGC AGCAGGACTA CCTGTCTCTG CCCCCTTGGG AGGTCAACAA
18451 GCCTGGGGAG GTGTGTTGAG ACCCCCAGGC CTAGACAGGC AAGGGGATGG
18501 AGAGGGCTTG CCTTCCCTCC CGCCTGACCT TCCTCAGTCA TTTCTGCAAA
18551 GCCAAGGGGC AGCCTCCTGT CAAGGTAGCT AGAGGCCTGG GAAAGGAGAT
18601 AGCCTTGCTC CGGCCCCCTT GACCTTCAGC AAATCACTTC TCTCCCTGCG
18651 CTCACACAGA CACACACACA CACACGTACA TGCACACATT TTTCCTGTCA
18701 GGTTAACTTA TTTGTAGGTT CTGCATTATT AGAACTTTCT AGATATACTC
18751 ATTCCATCTC CCCCTCATTT TTTTAATCAG GTTTCCTTGC TTTTGCCATT
18801 TTTCTTCCTT CTTTTTTCAC TGATTTATTA TGAGAGTGGG GCTGAGGTCT
18851 GAGCTGAGCC TTATCAGACT GAGATGCAGC TGGTTGTGTT GAGGACTTGT
18901 GTGGGCTGCC TGTCCCCGGC AGTCGCTGAT GCACATGACA TGATTCTCAT
18951 CTGGGTGCAG AGGTGGGAGG CACCAGGTGG GCACCCGTGG GGGTTAGGGC
19001 TTGGAAGAGT GGCACAGGAC TGGGCACGCT CAGTGAGGCT CAGGGAATTC
19051 AGACTAGCCT CGATTGTCAC TCCGAGAAAT GGGCATGGTA TTGGGGGTCG
19101 GGGGGGCGGT GCAAGGGACG CACATGAGAG ACTGTTTGGG AGCTTCTGGG
19151 GAGCCCTGCT AGTTGTCTCA GTGATGTCTG TGGGACCTCC AGTCCCTTGA
19201 GACCCCACGT CATGTAGAGA AGTTAACGGC CCAAGTGGTG GGCAGGCTGG
19251 TGGGACCTGG GGAACATCAG GAGAGGAGTC CAGAGCCCAC GTCTACTGCG
19301 GAAAAGTCAG GGGAAACTGC CAAACAAAGG AAAATGCCCC AAAGGCATAT
19351 ATGCTTTAGG GCCTTTGGTC CAAATGGCCC GGGTGGCCAC TCTTCCAGAT
19401 AGACCAGGCA ACTCTCCCTC CCACCGGCCA CAGATGAGGG GCTGCTGATC
19451 TATGCCTGGG CCTGCACCAG GGATTATGGT TCTTTTAAAT CTTTGCCTTT
19501 CAGATACAGG AAAAATAATG GCATTAAATT GCTTTAATTT GCATTATTTT
19551 AGTTATCCAG TTTGCACATA TTTTTATAGG TATCTTAGGC ATCGATTGGT
19601 ATTTTTTAAC TGGGCCAAGC CCATTAAGGT CTTTCTTCTG TTGGGTGCTA
19651 TCATTTTCCT GATTAAGTCT TTTTGACTAT TGACATACAG TCTTTCACAG
19701 ATGGTGGAGT GTTTTTCCCC CAAATCTGTT GTTTGTCTTA TAATGTTGTA
19751 TATGAGGTTT TATGGTGTAT GAATATGAAT GCTTCTGTAA TGTCAAACAG
19801 ATCCCTAGTA AACTCCTTCT TCACTTTTAC TGTCAGATTT ACAAAGGTCC
19851 TCCCATTGCA AAGCAGTGTT TGTCCTAATT TATATATTGT TTTTCTAGTT
19901 CATTTTGTGT TTCCAACTTT TCATGTAAAA TTTTAATTAT TTTTGAATGT
19951 GTGGATGTGA GACTGAGGTG CCTTTTGGTA CTGAAATTCT TTTTCCATGT
20001 ACCTGAAGTG TTACTTTTGT GATATAGGAA ATCCTTGTAT ATATACTTTA
20051 TTGGTCCCTA GGCTTCCTAT TTTGTTACCT TGCTTTCTCT ATGGCATCCA
20101 CCATTTTGAT TGTTCTACTT TTATGATATG TTTTCATAAG TGGTTAAGCA
20151 AGTATTCTCG TTACTTTTGC TCTTAAATCC CTATTCATTA CAGCAATGTT
20201 GGTGGTCAAA GAAAATGATA AACAACTTGA ATGTTCAATG GTCCTGAAAT
20251 ACATAACAAC ATTTTAGTAC ATTGTAAAGT AGAATCCTCT GTTCATAATG
20301 AACAAGATGA ACCAATGTGG ATTAGAAAGA AGTCCGAGAT ATTAATTCCA
20351 AAATATCCAG ACATTGTTAA AGGGAAAAAA TTGCAATAAA ATATTTGTAA
```

FIGURE 3F

```
20401 CATAAAACAA AGTGAAACCC TGAATTTGTG TGTGCATGTT GGTGTAGTTG
20451 GAGGAAGGGG TTGCTCTTTG AAACCTCAAT TGCTATTGTA AGTGATACAG
20501 CTCCAGTGAC TGGAGGAACA CCAGGGTCCT TAGTCTTGCG CCGATTTAAA
20551 TAAAACGACA CGGAAACACA TGGAGTGGTT TTAAGGAGTG GAGAGTTTAA
20601 TAGGCAAGAA AGAAGGAAGA AGCTCCCCTG TACAGAGACA GAGGGAGGGG
20651 GGATCCAAAG CTGAGAGAGG AAACCCTGAG TGCCACAGAA ATAAGCCAGT
20701 TATATGAGGA GGCTAGAGAA GGCAGTATCT GATTTGCATA GGGCTCAGGG
20751 GATTGGTTTG ACCAGGCATG TCATTCATGT AACCCCTGAA AAACCTGGCC
20801 CTTTCACCCT AGCATTTTAA TATGCAAATG CAGGGCGCCA TGATGTTCTA
20851 CACAGGTGGG ACTATGTGGG GGTGGCCATA TTGCCAGGCA AACATGGGGA
20901 CAAGGAAAAG ATGGCGGGAA TCCCCATGTT TGGGTGGACC CAGTTTCTAA
20951 CGGTCTGCAT TTGCATATCA AAGGTTGCCA GCCTGATTCT AAGAGCCGGG
21001 GCTTTCCTGC TAGACAAGAA ACGTTTTTTG GAGCTGCTTT TAAAACAGAA
21051 ACGAAAACTT CCCAAGGACC ACTTTTCCTC TTTATCTGCC TCAAATAATT
21101 TTTTAATAAT TCCTATAACA CAAGGAAATG AATTCTGCCA AACAGAAGGG
21151 CCTTTGGTCT TTGGGGCACT ACAGTGGGTA CATGATGGCG TGTGGAACAC
21201 CACGCAATGG AGGGAGACGC AGGGCACTCC TGGGAAAATC CAGGAGGGAT
21251 GAGGGAAGAG GAAAGACAGT GAGGGAAAGG AGGATAAAGA ACACACTTTT
21301 AAAAAATCGT TCATTATTAT CTGAAATTCC AACACAACTG AACGTCCTGT
21351 ATTTTTCCCT AGTCATGAGA GTGAAAAACT AAATAGAGAC TGAGTTCCCC
21401 ATACAAATAA CTGAGAGTGA TCGAGAGCTT ATTCCTGGCA GGCCCCATTC
21451 GAGTGACCTC TAAGATCAAT TCATTTAGAT ACTATGGAAG TGGAAGATAC
21501 TATCTTTATC ATTTTTGTCA TTGAGGAAAC TAAGGCACAG AGATGTCATA
21551 CAACTTGCCC CAGGTCTGCC AGCAGGTAAG GGGCAGAGCC AAGATTTGAA
21601 CTGTAGCCCT GTGTCTCAGA GCCTGCCCTC AAAAGGTAAG TCTCTCACCT
21651 AAAGATCCAT ACGGAGATGT AAGATGATCC ATGTTGGTTG GCAAGACGGA
21701 AAAATCCATA AACCAAATAA ATTGATTTGG TGGCAGGGGG AGATTGAATC
21751 AGAGGTGACC CTGAAAAGTG TCTGTTTATC TGGGAGCTGA ACACTGAAGG
21801 TGCAATTCTC ACCCATTGGA GTCCAGAGAG ACCTTCCCTG GAGGACTGCA
21851 GCTCCCTCAT CTGTCTTCCC CTGAGAACCC AGCCCAGAGC CATGCATGTA
21901 GTAGGTGATC ATTGAGGTGA GCAAGGCCTG CAGGAGGCTG TCCCTAAGAT
21951 GGAGGAGAAC AAAAAACT  (SEQ ID NO:3)
```

FEATURES:
Start:   2176
Exon:    2176-2251
Intron:  2252-3211
Exon:    3212-3335
Intron:  3336-5951
Exon:    5952-6142
Intron:  6143-9366
Exon:    9367-9524
Intron:  9525-9603
Exon:    9604-9772
Intron:  9773-10339
Exon:    10340-10475
Intron:  10476-10637
Exon:    10638-10795
Intron:  10796-12729
Exon:    12730-12869
Intron:  12870-13796
Exon:    13797-13959
Intron:  13960-15315
Exon:    15316-15406
Intron:  15407-15595
Exon:    15596-15653
Intron:  15654-16515
Exon:    16516-16619
Intron:  16620-17343
Exon:    17344-17513
Intron:  17514-18853
Exon:    18854-19197
Stop:    19198

CHROMOSOME MAP POSITION:
Chromosome 22

FIGURE 3G

ALLELIC VARIANTS (SNPs):

| DNA Position | Major | Minor | Domain | Protein Position | Major | Minor |
|---|---|---|---|---|---|---|
| 183 | C | T | Beyond ORF(5') | | | |
| 312 | G | T | Beyond ORF(5') | | | |
| 400 | T | C | Beyond ORF(5') | | | |
| 1449 | A | G T | Beyond ORF(5') | | | |
| 1453 | G | A | Beyond ORF(5') | | | |
| 2441 | T | C | Intron | | | |
| 2705 | T | C | Intron | | | |
| 2935 | G | A | Intron | | | |
| 3007 | T | G | Intron | | | |
| 5705 | G | C | Intron | | | |
| 5783 | A | G | Intron | | | |
| 6905 | G | - | Intron | | | |
| 7443 | A | - | Intron | | | |
| 7445 | G | - | Intron | | | |
| 7561 | C | T | Intron | | | |
| 7911 | T | C | Intron | | | |
| 9427 | C | - | Exon | 151 | T | |
| 13599 | C | T | Intron | | | |
| 13922 | T | C | Exon | 426 | S | S |
| 14005 | T | C | Intron | | | |
| 14702 | G | C | Intron | | | |
| 15228 | A | G | Intron | | | |
| 19251 | T | C | Beyond ORF(3') | | | |
| 21335 | T | C | Beyond ORF(3') | | | |
| 21698 | A | G | Beyond ORF(3') | | | |

Context:

DNA
Position
183
TGACTGTCGACCAATTACATAACATCCCACCCCTGTTTTCTCATCTACAAAGTGGAGCTT
CTAGTGGTAACCTATACATAGATGTATTCATATCCGTAAAACCTTTTGAATAATGCCTGG
CTCATGGAAAACACTGCAATATTGTCAGCCACTATCATGAATTCTCTCTGTGTATGTGAG
TA
[C,T]
TGTTTGTGCTCTTTGATGATATTGATTTGTTTTAACCTTTTAAAGTAAAAGACACTAACC
TGTCCTCCATAATTCTGGTTGGTATGGTCTATATGTTGAAGTGCACCCAAGTTTATGTTG
CAACCTAAGCCCCAATGTGAGAATATCTGGAGGTAGTGCCTGTGGCACCCTATAAAATAC
CCCAGCGAGCTCCCTTGCTTATTCCATGTGAGATTACAGGGAGAAGACTGCAAGGAACAG
GCCCTCACCAGATAGTGAATCTGCCCGCACCTTGATCTTGAACTTCCCAGCCTCCAGAAC 312
CAATTACATAACATCCCACCCCTGTTTTCTCATCTACAAAGTGGAGCTTCTAGTGGTAAC
CTATACATAGATGTATTCATATCCGTAAAACCTTTTGAATAATGCCTGGCTCATGGAAAA
CACTGCAATATTGTCAGCCACTATCATGAATTCTCTCTGTGTATGTGAGTACTGTTTGTG
CTCTTTGATGATATTGATTTGTTTTAACCTTTTAAAGTAAAAGACACTAACCTGTCCTCC
ATAATTCTGGTTGGTATGGTCTATATGTTGAAGTGCACCCAAGTTTATGTTGCAACCTAA
[G,T]
CCCCAATGTGAGAATATCTGGAGGTAGTGCCTGTGGCACCCTATAAAATACCCCAGCGAG
CTCCCTTGCTTATTCCATGTGAGATTACAGGGAGAAGACTGCAAGGAACAGGCCCTCACC
AGATAGTGAATCTGCCCGCACCTTGATCTTGAACTTCCCAGCCTCCAGAACTATGAGAAA
TAAACTTTGTTACTAGTAAGCCACTCCATCTATGGTATGTTGTTACAGTAGCCTAACGGA
TGAGTACATTGGTGCAAAGATTTTCTGTTTGCACTCCGTCCTTTCCTTTTATGGTTCAGT 400
AACCTTTTGAATAATGCCTGGCTCATGGAAAACACTGCAATATTGTCAGCCACTATCATG
AATTCTCTCTGTGTATGTGAGTACTGTTTGTGCTCTTTGATGATATTGATTTGTTTTAAC
CTTTTAAAGTAAAAGACACTAACCTGTCCTCCATAATTCTGGTTGGTATGGTCTATATGT
TGAAGTGCACCCAAGTTTATGTTGCAACCTAAGCCCCAATGTGAGAATATCTGGAGGTAG
TGCCTGTGGCACCCTATAAAATACCCCAGCGAGCTCCCTTGCTTATTCCATGTGAGATTA
[T,C]
AGGGAGAAGACTGCAAGGAACAGGCCCTCACCAGATAGTGAATCTGCCCGCACCTTGATC
TTGAACTTCCCAGCCTCCAGAACTATGAGAAATAAACTTTGTTACTAGTAAGCCACTCCA
TCTATGGTATGTTGTTACAGTAGCCTAACGGATGAGTACATTGGTGCAAAGATTTTCTGT
TTGCACTCCGTCCTTTCCTTTTATGGTTCAGTCAGTTTGACAAATTACAGAAGATTTCAC
TTTTATGTACTTCTGCCAGCCTTTGTCTCTGTGATGTCTCCTATGCTTTTAAGCTTAAAG

FIGURE 3H

1449    ATGTGTATATACATGTATGTATCTGTGTTGTTCATGTGTGTATGTGTGCCTGTGTCTCTG
TGTGTGTGTTTGTATGTGTGTGTGCATGTTTGTGTGTGTATATGTGTGTATATTGTATGT
ATCTGTGTGTGTCTGTGTCTGCCTCTGTGTGTGTGTCTGTGTGTGCATTTGTGTGTATAC
ATGTGGGTATGTGTGTGCATGTTTTGTGTGTACGTGTATATATGTATGTATCTGTGTGTG
TCTGTGTGTTGTGCGTGTGTGTGCCTGCATGTGTCCGTGTGCTTGTGTGTGTGTGTGTGT
[A,G,T]
TGCGTGGGCATCTTGAGTGAAGCTTCCAACAATCTAACAGAAGAAAAGGAGCCACACTTG
TCTGTTCTGCTCTCTTGGGTACTTCCCAGACCAGTGAAATGAAAGGGAGGAAACCCCCGG
CCTCCGAGGAGAAAAGGGAACTGGCAAGCAGAGGGTGGGGGATGACGGTAAAAGGAGCA
GGGGTGGGGAGAGCACAGGCCCTGTGGAAGTGAGGACATGTGTGTGTACATGTGTTCATG
TCCAGGGGATGACACTGTGGCATCCAACAGCCGTGGACCAGCAGCCCACGGGGAGCTTAG

1453    GTATATACATGTATGTATCTGTGTTGTTCATGTGTGTATGTGTGCCTGTGTCTCTGTGTG
TGTGTTTGTATGTGTGTGTGCATGTTTGTGTGTGTATATGTGTGTATATTGTATGTATCT
GTGTGTGTCTGTGTCTGCCTCTGTGTGTGTGTCTGTGTGTGCATTTGTGTGTATACATGT
GGGTATGTGTGTGCATGTTTTGTGTGTACGTGTATATATGTATGTATCTGTGTGTGTCTG
TGTGTTGTGCGTGTGTGTGCCTGCATGTGTCCGTGTGCTTGTGTGTGTGTGTGTGTTTGC
[G,A]
TGGGCATCTTGAGTGAAGCTTCCAACAATCTAACAGAAGAAAAGGAGCCACACTTGTCTG
TTCTGCTCTCTTGGGTACTTCCCAGACCAGTGAAATGAAAGGGAGGAAACCCCCGGCCTC
CGAGGAGAAAAGGGAACTGGCAAGCAGAGGGTGGGGGATGACGGTAAAAGGAGCAGGGG
TGGGGAGAGCACAGGCCCTGTGGAAGTGAGGACATGTGTGTGTACATGTGTTCATGTCCA
GGGGATGACACTGTGGCATCCAACAGCCGTGGACCAGCAGCCCACGGGGAGCTTAGTAGG

2441    GCTGGTGCCTGCCTGTCCAGAGCTGACCAGGGTAGATGGTGCTGGCCCAGGGGCTGCTCT
CCATGGCCCTGCTGGCCCTGTGCTGGGAGCGCAGCCTGGCAGGGGCAGAAGGTGAGTCCC
GTGGCTCCCACCCACTTCCCTGTCCCTGTCCTCACTGCTGCACCCTGGGGGAGGGCCGCA
GCGTATCCTCAGGATCCTGCCCGCCAGCCCTCCTCCTGCTCCCCTCCCTCTGTCTCTCCC
CCTGGCCTTCCCTGGGCCTCCCCCGCTTCCCTCCTCCTGCACATTCCTGCTCATCCTGTC
[T,C]
TGGAAAGTCCAGCTGAGCGTGTCTGGCTTCCTTGCCCACATTTCTCAGGGCGGCACTCCC
GGCCCCTAGGCTCCAGGATGGCTGCTCTGGCCGTTTCCCTGCCCCTCCTTCCCCAGCAGA
CACTCTCTGTGCCTCAGTGGTTCCCACCTCCGGGACTTTGCTCCTGCAGGGCCTTGGCTG
GGGTTCTCTCCCTGCTTCAGCCGCTAGCACCCTCCTTGTGCCTGAAGCCCGCACTGGGAT
GCTCCTGGGCTCTTGAGGTGAAATGGCCCCTCCCAAGGGCTCCCAGAGACCTGGCTTCTG

2705    GCTTCCCTCCTCCTGCACATTCCTGCTCATCCTGTCTTGGAAAGTCCAGCTGAGCGTGTC
TGGCTTCCTTGCCCACATTTCTCAGGGCGGCACTCCCGGCCCCTAGGCTCCAGGATGGCT
GCTCTGGCCGTTTCCCTGCCCCTCCTTCCCCAGCAGACACTCTCTGTGCCTCAGTGGTTC
CCACCTCCGGGACTTTGCTCCTGCAGGGCCTTGGCTGGGGTTCTCTCCCTGCTTCAGCCG
CTAGCACCCTCCTTGTGCCTGAAGCCCGCACTGGGATGCTCCTGGGCTCTTGAGGTGAAA
[T,C]
GGCCCCTCCCAAGGGCTCCCAGAGACCTGGCTTCTGTGATAATGCTGGGACCACAGTCCC
CTTAACAAATACCAGGCTCCTGAGGACGGGGACTAGAGAGGAGGTGGGAGGTTGCAGGGT
AGAACTCTGCCACGCTGCATCCCAGGGCTGAGTGTGTGCCCCCTCCCAGGCTGCACAGTC
GGTCCAGGGGCCAGGCCTGTGCTTGATGCATGTCCCTGTCCTGGGGTGGGGGGAGGGGAC
CGTGCCCAGGAACAGCACACTGCGGAGGCCCAGAAACCATGCTGAGAACCAACAGAATGT

2935    GCTTCAGCCGCTAGCACCCTCCTTGTGCCTGAAGCCCGCACTGGGATGCTCCTGGGCTCT
TGAGGTGAAATGGCCCCTCCCAAGGGCTCCCAGAGACCTGGCTTCTGTGATAATGCTGGG
ACCACAGTCCCCTTAACAAATACCAGGCTCCTGAGGACGGGGACTAGAGAGGAGGTGGGA
GGTTGCAGGGTAGAACTCTGCCACGCTGCATCCCAGGGCTGAGTGTGTGCCCCCTCCCAG
GCTGCACAGTCGGTCCAGGGGCCAGGCCTGTGCTTGATGCATGTCCCTGTCCTGGGGTGG
[G,A]
GGGAGGGGACCGTGCCCAGGAACAGCACACTGCGGAGGCCCAGAAACCATGCTGAGAACC
AACAGAATGTCTTGCTTCTGCCAGGAGAGGAGGGTCCGCAACCAGGAGCCCACCCCGGCA
GACATGAACACATGTACATGTGCCTGGCCACCTGGTGCCTCTGCAGGGACCTGGGAGACC
CCTCCCCAGAGCGGGACATCCCAAAGCAGCTGGGGGTGATGGTGACAAGGGTCCCTGCAG
GAAAGAGAGGTGACCCCCTTCTACCCCTCTTGTCAGAAACCATCCCGCTGCAGACCCTGC

3007    GCCCCTCCCAAGGGCTCCCAGAGACCTGGCTTCTGTGATAATGCTGGGACCACAGTCCCC
TTAACAAATACCAGGCTCCTGAGGACGGGGACTAGAGAGGAGGTGGGAGGTTGCAGGGTA
GAACTCTGCCACGCTGCATCCCAGGGCTGAGTGTGTGCCCCCTCCCAGGCTGCACAGTCG
GTCCAGGGGCCAGGCCTGTGCTTGATGCATGTCCCTGTCCTGGGGTGGGGGGAGGGGACC
GTGCCCAGGAACAGCACACTGCGGAGGCCCAGAAACCATGCTGAGAACCAACAGAATGTC
[T,G]
TGCTTCTGCCAGGAGAGGAGGGTCCGCAACCAGGAGCCCACCCCGGCAGACATGAACACA

FIGURE 3I

```
       TGTACATGTGCCTGGCCACCTGGTGCCTCTGCAGGGACCTGGGAGACCCCTCCCCAGAGC
       GGGACATCCCAAAGCAGCTGGGGGTGATGGTGACAAGGGTCCCTGCAGGAAAGAGAGGTG
       ACCCCCTTCTACCCCTCTTGTCAGAAACCATCCCGCTGCAGACCCTGCGCTGCTACAACG
       ACTACACCAGCCACATCACCTGCAGGTGGGCAGACACCCAGGATGCCCAGCGGCTCGTCA

5705   GCTCATGACTGTTTCCCACTCACTCGCAGTGAGATCCAATCCCATCATGTAGATGGATGG
       GTCTCCTAGACCTCCCTATCACACGCTCTACTCCCTGCGCACTGGTTTTAGGCCAAGCCA
       CGCAGCACACCAAACTCTGCCTGTCCCAGGGCCTTTGCACGTGCTGTTCCCATTTCCTGA
       AATCCTCACAATTTGCACAGTCCCTCCCTCAATGCCTTTAACATTCTGCCCCCAGGTCAC
       CTCCTTAGAGAAGCCTGCTTGTCCCATATTTCAAATTGCCTCCCTGGCCCAGCCCTTCCT
       [G,C]
       CCTCCTCACCTGCTTCTTGCTTTATTTTTCCACATGAAGTTCTCTCCACTGCACACGCTA
       CACACTTTGTTCCATGCAGGTCCCCTTCTCCCAGGATGGCAGCTCCGTGGGCAGGATTTT
       TGTGTGTTTTATCACTGCTGGCCCCTGATTCTGAACAGAGCCAGGCATGTGGTGAGCACT
       CGAGGAACCTTTCGTGAGTCAGTGATACCCATACACCCTGGGCTAAGCCGTGTCCTCTCC
       CAACAGGGACCTCCTGGAGCCAGTGTCCTGTGACCTCAGTGATGACATGCCCTGGTCAGC

5783   TCACACGCTCTACTCCCTGCGCACTGGTTTTAGGCCAAGCCACGCAGCACACCAAACTCT
       GCCTGTCCCAGGGCCTTTGCACGTGCTGTTCCCATTTCCTGAAATCCTCACAATTTGCAC
       AGTCCCTCCCTCAATGCCTTTAACATTCTGCCCCCAGGTCACCTCCTTAGAGAAGCCTGC
       TTGTCCCATATTTCAAATTGCCTCCCTGGCCCAGCCCTTCCTGCCTCCTCACCTGCTTCT
       TGCTTTATTTTTCCACATGAAGTTCTCTCCACTGCACACGCTACACACTTTGTTCCATGC
       [A,G]
       GGTCCCCCTTCTCCCAGGATGGCAGCTCCGTGGGCAGGATTTTTGTGTGTTTTATCACTGC
       TGGCCCCTGATTCTGAACAGAGCCAGGCATGTGGTGAGCACTCGAGGAACCTTTCGTGAG
       TCAGTGATACCCATACACCCTGGGCTAAGCCGTGTCCTCTCCCAACAGGGACCTCCTGGA
       GCCAGTGTCCTGTGACCTCAGTGATGACATGCCCTGGTCAGCCTGCCCCCATCCCCGCTG
       CGTGCCCAGGAGATGTGTCATTCCCTGCCAGAGTTTTGTCGTCACTGACGTTGACTACTT

6905   AGGGAGCTTGTCTCCTCGCTGCCCTGGAGGAGGGGCCCCGGTGTGGGCCGAAATCCCACA
       GTGGTCCATGAAGCCATCTGTGGTCTAGGGTGGGGTAGATGATTATTTTATGTAGTTAGG
       TTTTATTTGCCTCTATATTAGAAAGAAATATAACCTGCACTTCGAAGTCCTGGATTCAAG
       GAAATGGTTGCTTAGAATGAAGCTAAACCTGAAAAGGGACACGTTTTATGAAAGTTTTCG
       TTGACGTGGCAAAAACCCATGCTGGTGGCAGGCTGGTAGGAGGTACTGCAGGCTGTCATT
       [G,-]
       GGAGTCTCAGAACCACGGCAGGCTTGGTGCTGTTATTGGTGCCTTTGGCTGCTGCTGAAA
       CGGAGACAGAGGGAGGTGACTAGTCCAAGGCCTCTCTACTGCTGCTGGCAGAGCTGAGAT
       CCAGTGCAGGATGGTCTGAGTCCCCGGTCCTAACCACCGAACCACCTGGTGCTCTTTGCA
       AGGGTCACACGGAAGGGGCTCTGACCATGGCTTCCTGCCCTTTTTTGCCACAACATCATA
       AAGCCACTGCCAGAGGAGGGGATCAGTTAGGCCACCAGGAGTCCATCAGAAGCAACATTT

7443   ATAAAGCCACTGCCAGAGGAGGGGATCAGTTAGGCCACCAGGAGTCCATCAGAAGCAACA
       TTTCCACACATGGGTTTGATGGACACGAGAGTCCCTTCCTTCCCGAATGGAGCTCAGGGG
       GCCCAGGCTGGAGGGAGGGGAAACACTGTATGCCGTCCACCGTGAGAACTTACTGACAGT
       GGCGGGTGGGTGCCTCATGCAGGGGGTAAAGGGCAGGGCCCCTGGGAGATCAGAACAGGC
       TTCCCAGAGGGAAGAGCTTTGCAACTCAGATCTGAAGGGTAGACAGGAGGGGAGGGCAGT
       [A,-]
       AGAGCCTCTCTGGCAGGGTAACAGCTGTGCAGAGGCTGGGGGATCAGAAGGGCATGGGCA
       GCTGGGGAACCTGCTCACCATTGTGTCCAGGGAGCATCAGCTTCAAGGGCTGGACAGCGG
       TGGGAAGAAGCAGGAGACACAGGTAAGGACCTGTCCCTGGAGAGGCTTCTGTCTCCTGCA
       GTCTCAGGTAGAGGGGACCCTCTAGGCATGGAGAGCACTGAGGGGAAATGACATGATCAG
       ATGTGGATGTGAGAATGCTGGGGACAGGGGACTTACAGGGTAGATTGGAGGAGCATTAGT

7445   AAAGCCACTGCCAGAGGAGGGGATCAGTTAGGCCACCAGGAGTCCATCAGAAGCAACATT
       TCCACACATGGGTTTGATGGACACGAGAGTCCCTTCCTTCCCGAATGGAGCTCAGGGGGC
       CCAGGCTGGAGGGAGGGGAAACACTGTATGCCGTCCACCGTGAGAACTTACTGACAGTGG
       CGGGTGGGTGCCTCATGCAGGGGGTAAAGGGCAGGGCCCCTGGGAGATCAGAACAGGCTT
       CCCAGAGGGAAGAGCTTTGCAACTCAGATCTGAAGGGTAGACAGGAGGGGAGGGCAGTAA
       [G,-]
       AGCCTCTCTGGCAGGGTAACAGCTGTGCAGAGGCTGGGGGATCAGAAGGGCATGGGCAGC
       TGGGGAACCTGCTCACCATTGTGTCCAGGGAGCATCAGCTTCAAGGGCTGGACAGCGGTG
       GAAGAAGCAGGAGACACAGGTAAGGACCTGTCCCTGGAGAGGCTTCTGTCTCCTGCAGT
       CTCAGGTAGAGGGGACCCTCTAGGCATGGAGAGCACTGAGGGGAAATGACATGATCAGAT
       GTGGATGTGAGAATGCTGGGGACAGGGGACTTACAGGGTAGATTGGAGGAGCATTAGTTG

7561   GGGCCCAGGCTGGAGGGAGGGGAAACACTGTATGCCGTCCACCGTGAGAACTTACTGACA
       GTGGCGGGTGGGTGCCTCATGCAGGGGGTAAAGGGCAGGGCCCCTGGGAGATCAGAACAG
       GCTTCCCAGAGGGAAGAGCTTTGCAACTCAGATCTGAAGGGTAGACAGGAGGGGAGGGCA
```

FIGURE 3J

```
       GTAAGAGCCTCTCTGGCAGGGTAACAGCTGTGCAGAGGCTGGGGGATCAGAAGGGCATGG
       GCAGCTGGGGAACCTGCTCACCATTGTGTCCAGGGAGCATCAGCTTCAAGGGCTGGACAG
       [C,T]
       GGTGGGAAGAAGCAGGAGACACAGGTAAGGACCTGTCCCTGGAGAGGCTTCTGTCTCCTG
       CAGTCTCAGGTAGAGGGGACCCTCTAGGCATGGAGAGCACTGAGGGGAAATGACATGATC
       AGATGTGGATGTGAGAATGCTGGGGACAGGGGACTTACAGGGTAGATTGGAGGAGCATTA
       GTTGGGAAAGAAGTTGAAATTCAGGCTGTGGCCTAAAGCACTCATTCCTAGAAATGATGA
       GGACACAACTGGCTAGGAGATGGGGACATGAGGGCATGCAAATCATAGTTCAGATATACA

7911   TCTGTCTCCTGCAGTCTCAGGTAGAGGGGACCCTCTAGGCATGGAGAGCACTGAGGGGAA
       ATGACATGATCAGATGTGGATGTGAGAATGCTGGGGACAGGGGACTTACAGGGTAGATTG
       GAGGAGCATTAGTTGGGAAAGAAGTTGAAATTCAGGCTGTGGCCTAAAGCACTCATTCCT
       AGAAATGATGAGGACACAACTGGCTAGGAGATGGGGACATGAGGGCATGCAAATCATAGT
       TCAGATATACACACAATTCATTCATTCAACCTTCTTTCCTTGAGCGCCTACATAAGCCAA
       [T,C]
       GAAGCAGTCAACAAACCAGCCAGCAACCCTGCCCTTGGAGCTTACAGCCTGGAAACAAGG
       AAGGTTTCTAAGGCGATGGAGACAACTTAGATATAGGGAGAGAAGTGTGGCCCTTGGCCT
       CCTGGAGCCTGTGTTGAGTAGCGAGGTAGGGTCCAGCCTAATGCAGATTAGCAATGAATC
       AAGGATGCTGGGAGGTACTGGGCAGGCGACAGGCATGCATCTGATCTGCTCTGAGTCTCC
       ATGTTTGGAGACCTTGGACATTTTACTTCCTCTATGAGTTTCTCCGTCTGTGAAATGAGC

9427   GAGTTCGGGTCACGTGCGCATTGCAATCTGCACGGCTTTCCATTGCTTTCATGTTGAAAC
       CCTACAGTTTTGCAGATGAAGGGCTGAGGCTCACAGAGGAGACGGGTCTTGCTCAAGGTC
       CCTCAGCTGCTGGGGGCAGGGGTGGCCTGGAACCCCCTGTGTCCACACAAAAGGCCATGC
       AGGCCCTGACTGCCCCCCAGCGGTCCAGCCCTTAGGTGCCCTTCACTTCCTCCCCTCCAG
       TCCAGCCTCCTGAGCCCAGGGACCTGCAGATCAGCACCGACCAGGACCACTTCCTGCTGA
       [C,-]
       CTGGAGTGTGGCCCTTGGGAGTCCCCAGAGCCACTGGTTGTCCCCAGGGGATCTGGAGTT
       TGAGGTGGTCTACAAGCGGCTTCAGGACTCTTGGGAGGTAGGAACCACGGCCAGCTCTGC
       CCCAGCCCGAAGGGATGGGCAGCACCCCTCCTCCAGCACCCACTGTCTCCTGACAGGACG
       CAGCCATCCTCCTCTCCAACACCTCCCAGGCCACCCTGGGGCCAGAGCACCTCATGCCCA
       GCAGCACCTACGTGGCCCGAGTACGGACCCGCCTGGCCCCAGGTTCTCGGCTCTCAGGAC

13599  CACAGAGCCCAGAACAGAAACCACAGAACCAACCCCACACCTTCAGTCTAGAAATGGGGC
       AACTGAGGCTAGGAGGGAGGTGGGCCAGTGGTGGAGCCAGGAGCGGGCCCTGGGGTCCTG
       AACCCCCATTCTCAGGGTCCAGAGTCCAGTCGGCCTGCACTGCGTTCCTGAAAAGGCCAC
       AATATGGGTGCAAGCTGCCCCAGAAGGGCTGGGAGCTGAGAAGGCTCAAAATAGGGTGGG
       ACAGGTGGCTTCAGGGTTCTGGGCCTCAGTGTTGTCAATGTCAGGGGCTGCACTGACAGG
       [C,T]
       GGAGTCCCCGGTGCCATCCGAAGTGCTGTCCGTGGGTGGGCCCTCAGGGAGGATCCACGG
       TGGTGAGAGAGAAGCCGCAGCAGGCCTGGGGTATGGCAGGAGCTAGGAGCCAGCGAAGCC
       GAGGGTCCAGGTGGGAGGGATTTGCAGCTGCTCCCACGGGCACCGGGCCAGGCCTCACCC
       TCAGTGCCAACCCACAGGACAGCAAGACCGAGACCCTCCAGAACGCCCACAGCATGGCCC
       TGCCAGCCCTGGAGCCCTCCACCAGGTACTGGGCCAGGGTGAGGGTCAGGACCTCCCGCA

13922  GTGCTGTCCGTGGGTGGGCCCTCAGGGAGGATCCACGGTGGTGAGAGAGAAGCCGCAGCA
       GGCCTGGGGTATGGCAGGAGCTAGGAGCCAGCGAAGCCGAGGGTCCAGGTGGGAGGGATT
       TGCAGCTGCTCCCACGGGCACCGGGCCAGGCCTCACCCTCAGTGCCAACCCACAGGACAG
       CAAGACCGAGACCCTCCAGAACGCCCACAGCATGGCCCTGCCAGCCCTGGAGCCCTCCAC
       CAGGTACTGGGCCAGGGTGAGGGTCAGGACCTCCCGCACCGGCTACAACGGGATCTGGAG
       [T,C]
       GAGTGGAGTGAGGCGCGCTCCTGGGACACCGAGTCGGGTAGGTGAAGGCTGGAGTCCAGA
       GCTTCTGGCCAGGACCAGCTCATAGTTTCTCACTGCCAGAAAATCCCCAATGCAGCAGCC
       GTAGCAGGCCTGCAACAACTTGTAGGTGAGCCGTCTCCCCGATTAGATGGTGGCCAAAGA
       GAAAGGGAAGGCCTTTGCAGAGAGCACCTCCCACCTGGTCATCAGACCCGCAAGTTGAAA
       GAGGCAAAGGGTAAAGCAGGCAGAAACTGGGCGTGGAGTCAGAAGTTCTCCACCCACTCT

14005  GGAGCCAGCGAAGCCGAGGGTCCAGGTGGGAGGGATTTGCAGCTGCTCCCACGGGCACCG
       GGCCAGGCCTCACCCTCAGTGCCAACCCACAGGACAGCAAGACCGAGACCCTCCAGAACG
       CCCACAGCATGGCCCTGCCAGCCCTGGAGCCCTCCACCAGGTACTGGGCCAGGGTGAGGG
       TCAGGACCTCCCGCACCGGCTACAACGGGATCTGGAGTGAGTGGAGTGAGGCGCGCTCCT
       GGGACACCGAGTCGGGTAGGTGAAGGCTGGAGTCCAGAGCTTCTGGCCAGGACCAGCTCA
       [T,C]
       AGTTTCTCACTGCCAGAAAATCCCCAATGCAGCAGCCGTAGCAGGCCTGCAACAACTTGT
       AGGTGAGCCGTCTCCCCGATTAGATGGTGGCCAAAGAGAAAGGGAAGGCCTTTGCAGAGA
       GCACCTCCCACCTGGTCATCAGACCCGCAAGTTGAAAGAGGCAAAGGGTAAAGCAGGCAG
       AAACTGGGCGTGGAGTCAGAAGTTCTCCACCCACTCTTCATGAGACAGCACAGCTGGGCA
       GAGGATGCCACATCTCTGGGTGGGCACAGAGATGTGGGGCTCCAGACCCCACTCCACTCA
```

FIGURE 3K

14702   AGGTCTCATGATCGCTCCTCCTTTAAACTGGGACTTAGGCTTCTGTTAATATGGCCCTTG
        GTTTCTTAGCTTTTGGGACTACCAAGTTTTTGTGGTTGCTCAGCCCGAGTTTCCTGTTAC
        CATGGAAGCAAGAAAATCTAGAGCCACAGACTGGGTCCTTGGATTGGAAGGTTTTGCTGT
        GATTCCTTCATCTTCCCACCTCCCTGCACTTGCTGCGTGCACTGACCCCTCACCTTTCAC
        CATAGTGACCACCAGGCGACTCCCGCAGAACAAGACAAGTCCAAGGGGTGGTTTCAGAGA
        [G,C]
        AGTAAGGATACAGGAGATATTGGGAGCAACCCAAGTCCCCAGCCAGGCTTGGTAGCGGCA
        GGGGCCCAGGGAGAGGGCCACAACCAGGTAGAAAGGAGGCCGGACCAATGGGCCCAAGAG
        AGGAGGAAGAGGGGAGTCCTGGAGGAACCTGGCCTGGGAGCTCAGGGCTGGGCAGCAGGT
        GGGATCAGGGGCCTCTGGAGGGGCCTTTGCTCCTGCTGGTGCCTCTGCCACTATGCCTTT
        CCCCATCTCCACCTCTAATCCTTCCTATTACTGGAGGCCCAGCTAATATGCCACCTCCTT

15228   TGCCACTATGCCTTTCCCCATCTCCACCTCTAATCCTTCCTATTACTGGAGGCCCAGCTA
        ATATGCCACCTCCTTCAGGAAGTCCCCTGTGATTGCCATGAACAGTGGTTCTTGCCCTCC
        CTGTAGCACCTCCTGTGCTATAGATCCTGGAAAGGATCTGACCCTCCTGTGTCCTCCCAG
        CACTTTGAACACTGTGGGGGTTCAGACCAATGCCCTTCCCAGCATGGATCTGGCCTCTCT
        CCCCTAATCCCCCAAGGCAGTAAGTTCCAGAGCCCTGGGCCTGCACAGAGCGGGGTCTTA
        [A,G]
        GGAATACTGCACCAACCCCACTCCCTGCCCTGAGGTCGATTTCCCGCCCAGATGCTGACA
        TTCCTCTTTCTCCCCGGCTGCTGGAAGTGCTGCCTATGTGGGTGCTGGCCCTCATCGTGA
        TCTTCCTCACCATCGCTGTGCTCCTGGCCCTCCGCTTCTGTGGCATCTACGGGTACAGGT
        GAGGGGACTCTGTGGGGCTGGAGGTGGCAGCCGAGACCCCAGAGGGCACTGGGGAATCCC
        ACCCAGCTCCCTCCAGGCCCTGCTCTGCCGCTCCCTTCCTGGGCCTCAGTTTCCCCTCTG

19251   CTGGGTGCAGAGGTGGGAGGCACCAGGTGGGCACCCGTGGGGGTTAGGGCTTGGAAGAGT
        GGCACAGGACTGGGCACGCTCAGTGAGGCTCAGGGAATTCAGACTAGCCTCGATTGTCAC
        TCCGAGAAATGGGCATGGTATTGGGGGTCGGGGGGGCGGTGCAAGGGACGCACATGAGAG
        ACTGTTTGGGAGCTTCTGGGGAGCCCTGCTAGTTGTCTCAGTGATGTCTGTGGGACCTCC
        AGTCCCTTGAGACCCCACGTCATGTAGAGAAGTTAACGGCCCAAGTGGTGGGCAGGCTGG
        [T,C]
        GGGACCTGGGGAACATCAGGAGAGGAGTCCAGAGCCCACGTCTACTGCGGAAAAGTCAGG
        GGAAACTGCCAAACAAAGGAAAATGCCCCAAAGGCATATATGCTTTAGGGCCTTTGGTCC
        AAATGGCCCGGGTGGCCACTCTTCCAGATAGACCAGGCAACTCTCCCTCCCACCGGCCAC
        AGATGAGGGCTGCTGATCTATGCCTGGGCCTGCACCAGGGATTATGGTTCTTTTAAATC
        TTTGCCTTTCAGATACAGGAAAAATAATGGCATTAAATTGCTTTAATTTGCATTATTTTA

21335   TGCTTTTAAAACAGAAACGAAAACTTCCCAAGGACCACTTTTCCTCTTTATCTGCCTCAA
        ATAATTTTTTAATAATTCCTATAACACAAGGAAATGAATTCTGCCAAACAGAAGGGCCTT
        TGGTCTTTGGGGCACTACAGTGGGTACATGATGGCGTGTGGAACACCACGCAATGGAGGG
        AGACGCAGGGCACTCCTGGGAAAATCCAGGAGGGATGAGGGAAGAGGAAAGACAGTGAGG
        GAAAGGAGGATAAAGAACACACTTTTAAAAAAATCGTTCATTATTATCTGAAATTCCAACA
        [T,C]
        AACTGAACGTCCTGTATTTTTCCCTAGTCATGAGAGTGAAAAACTAAATAGAGACTGAGT
        TCCCCATACAAATAACTGAGAGTGATCGAGAGCTTATTCCTGGCAGGCCCCATTCGAGTG
        ACCTCTAAGATCAATTCATTTAGATACTATGGAAGTGGAAGATACTATCTTTATCATTTT
        TGTCATTGAGGAAACTAAGGCACAGAGATGTCATACAACTTGCCCCAGGTCTGCCAGCAG
        GTAAGGGGCAGAGCCAAGATTTGAACTGTAGCCCTGTGTCTCAGAGCCTGCCCTCAAAAG

21698   CCCATACAAATAACTGAGAGTGATCGAGAGCTTATTCCTGGCAGGCCCCATTCGAGTGAC
        CTCTAAGATCAATTCATTTAGATACTATGGAAGTGGAAGATACTATCTTTATCATTTTTG
        TCATTGAGGAAACTAAGGCACAGAGATGTCATACAACTTGCCCCAGGTCTGCCAGCAGGT
        AAGGGGCAGAGCCAAGATTTGAACTGTAGCCCTGTGTCTCAGAGCCTGCCCTCAAAAGGT
        AAGTCTCTCACCTAAAGATCCATACGGAGATGTAAGATGATCCATGTTGGTTGGCAAGAC
        [A,G]
        GAAAAATCCATAAACCAAATAAATTGATTTGGTGGCAGGGGGAGATTGAATCAGAGGTGA
        CCCTGAAAAGTGTCTGTTTATCTGGGAGCTGAACACTGAAGGTGCAATTCTCACCCATTG
        GAGTCCAGAGAGACCTTCCCTGGAGGACTGCAGCTCCCTCATCTGTCTTCCCCTGAGAAC
        CCAGCCCAGAGCCATGCATGTAGTAGGTGATCATTGAGGTGAGCAAGGCCTGCAGGAGGC
        TGTCCCTAAGATGGAGGAGAACAAAAAAACT

FIGURE 3L

SEQUENCE LISTING

<160> NUMBER OF SEQ ID NOS: 4

<210> SEQ ID NO 1
<211> LENGTH: 3394
<212> TYPE: DNA
<213> ORGANISM: Human

<400> SEQUENCE: 1

```
ctcccaccac acagaggcct ggaggaggca gaggccagga gggagaggtc ccaagagcct      60
gtgaaatggg tctggcctgg ctcccagctg ggcaggaaca caggacttca ggatactaag     120
gaccctgtca tgcccatggc cagcacccac cagtgctggt gcctgcctgt ccagagctga     180
ccagggagat ggtgctggcc caggggctgc tctccatggc cctgctggcc ctgtgctggg     240
agcgcagcct ggcaggggca gaagaaacca tcccgctgca gaccctgcgc tgctacaacg     300
actacaccag ccacatcacc tgcaggtggg cagacaccca ggatgcccag cggctcgtca     360
acgtgaccct cattcgccgg gtgaatgagg acctcctgga gccagtgtcc tgtgacctca     420
gtgatgacat gccctggtca gcctgccccc atccccgctg cgtgcccagg agatgtgtca     480
ttccctgcca gagttttgtc gtcactgacg ttgactactt ctcattccaa ccagacaggc     540
ctctgggcac ccggctcacc gtcactctga cccagcatgt ccagcctcct gagcccaggg     600
acctgcagat cagcaccgac caggaccact tcctgctgac ctggagtgtg gcccttggga     660
gtccccagag ccactggttg tccccagggg atctggagtt tgaggtggtc tacaagcggc     720
ttcaggactc ttgggaggac gcagccatcc tcctctccaa cacctcccag gccaccctgg     780
ggccagagca cctcatgccc agcagcacct acgtggcccg agtacggacc cgcctggccc     840
caggttctcg gctctcagga cgtcccagca agtggagccc agaggtttgc tgggactccc     900
```

-continued

| | | | |
|---|---|---|---|
| agccagggga | tgaggcccag | ccccagaacc | tggagtgctt ctttgacggg gccgccgtgc | 960 |
| tcagctgctc | ctgggaggtg | aggaaggagg | tggccagctc ggtctccttt ggcctattct | 1020 |
| acaagcccag | cccagatgca | ggggaggaag | agtgctcccc agtgctgagg gagggctcg | 1080 |
| gcagcctcca | caccaggcac | cactgccaga | ttcccgtgcc cgaccccgcg acccacggcc | 1140 |
| aatacatcgt | ctctgttcag | ccaaggaggg | cagagaaaca cataaagagc tcagtgaaca | 1200 |
| tccagatggc | ccctccatcc | ctcaacgtga | ccaaggatgg agacagctac agcctgcgct | 1260 |
| gggaaacaat | gaaaatgcga | tacgaacaca | tagaccacac atttgagatc cagtacagga | 1320 |
| aagacacggc | cacgtggaag | gacagcaaga | ccgagaccct ccagaacgcc cacagcatgg | 1380 |
| ccctgccagc | cctggagccc | tccaccaggt | actgggccag ggtgagggtc aggacctccc | 1440 |
| gcaccggcta | caacgggatc | tggagcgagt | ggagtgaggc gcgctcctgg acaccgagt | 1500 |
| cggtgctgcc | tatgtgggtg | ctggccctca | tcgtgatctt cctcaccatc gctgtgctcc | 1560 |
| tggccctccg | cttctgtggc | atctacgggt | acaggctgcg cagaaagtgg gaggagaaga | 1620 |
| tccccaaccc | cagcaagagc | cacctgttcc | agaacgggag cgcagagctt tggcccccag | 1680 |
| gcagcatgtc | ggccttcact | agcgggagtc | ccccacacca ggggccgtgg ggcagccgct | 1740 |
| tccctgagct | ggaggggtg | ttccctgtag | gattcgggga cagcgaggtg tcacctctca | 1800 |
| ccatagagga | ccccaagcat | gtctgtgatc | caccatctgg gcctgacacg actccagctg | 1860 |
| cctcagatct | acccacagag | cagccccca | gccccagcc aggcccgcct gccgcctccc | 1920 |
| acacacctga | gccttatcag | actgagatgc | ggctggttgt gttgaggact tgtgtgggct | 1980 |
| gcctgtcccc | ggcagtcgct | gatgcacatg | acatgattct catctgggtg cagaggtggg | 2040 |
| aggcaccagg | tgggcacccg | tggggttag | ggcttggaag agtggcacag gactgggcac | 2100 |
| gctcagtgag | gctcagggaa | ttcagactag | cctcgattgt cactccgaga atgggcatg | 2160 |
| gtattggggg | tcggggggc | ggtgcaaggg | acgcacatga gagactgttt gggagcttct | 2220 |
| ggggagccct | gctagttgtc | tcagtgatgt | ctgtgggacc tccagtccct tgagacccca | 2280 |
| cgtcatgtag | agaagttaac | ggcccaagtg | gtgggcaggc tggcgggacc tggggaacat | 2340 |
| caggagagga | gtccagagcc | cacgtctact | gcggaaaagt caggggaaac tgccaaacaa | 2400 |
| aggaaaatgc | cccaaaggca | tatatgcttt | agggcctttg gtccaaatgg cccggtggc | 2460 |
| cactcttcca | gatagaccag | gcaactctcc | ctcccaccgg ccacagatga ggggctgctg | 2520 |
| atctatgcct | gggcctgcac | cagggattat | ggttctttta aatctttgcc tttcagatac | 2580 |
| aggaaaaata | atggcattaa | attgctttaa | tttgcattat tttagttatc cagtttgcac | 2640 |
| atattttat | aggtatctta | ggcatcgatt | ggtattttt aactgggcca agcccattaa | 2700 |
| ggtctttctt | ctgttgggtg | ctatcatttt | ctgattaagt cttttgact attgacatac | 2760 |
| agtctttcac | agatggtgga | gtgttttcc | cccaaatctg ttgtttgtct tataatgttg | 2820 |
| tatatgaggt | tttatggtgt | atgaatatga | atgcttctgt aatgtcaaac agatccctag | 2880 |
| taaactcctt | cttcactttt | actgtcagat | ttacaaaggt cctcccattg caaagcagtg | 2940 |
| tttgtcctaa | ttcatatatc | gtttttctag | tccatttgt gtttccaacc ctttatgtaa | 3000 |
| aatcttaatt | atttcttgaa | tgtgtggatg | tgaaactgag gcggcctttc cggaactgaa | 3060 |
| atacttataa | gacatgaccc | gtgtgagtga | cacttttgc ggattcatga acactcctcc | 3120 |
| cgttcatctc | cgttccccgc | ccccccatgc | gttaattttc tttttatttt tagacgttga | 3180 |
| cggcagccag | cttacccgcc | gtcttttatc | ttggtcccca cctcgagttc cgccccgcat | 3240 |
| agtgttaacc | ggacgcgccc | tccagccgtc | cctggaccgt atccatgtac ttgtattcct | 3300 | acaccgcccc ttctgccgcc accacaataa agtggctaca aatgtattgc atgcgagcgc    3360 acccttttac cccctctgc ctgacgcgcc cccc    3394

<210> SEQ ID NO 2
<211> LENGTH: 694
<212> TYPE: PRT
<213> ORGANISM: Human

<400> SEQUENCE: 2

```
Met Val Leu Ala Gln Gly Leu Leu Ser Met Ala Leu Ala Leu Cys
 1               5                  10                  15

Trp Glu Arg Ser Leu Ala Gly Ala Glu Glu Thr Ile Pro Leu Gln Thr
                20                  25                  30

Leu Arg Cys Tyr Asn Asp Tyr Thr Ser His Ile Thr Cys Arg Trp Ala
                35                  40                  45

Asp Thr Gln Asp Ala Gln Arg Leu Val Asn Val Thr Leu Ile Arg Arg
 50                  55                  60

Val Asn Glu Asp Leu Leu Glu Pro Val Ser Cys Asp Leu Ser Asp Asp
 65                  70                  75                  80

Met Pro Trp Ser Ala Cys Pro His Pro Arg Cys Val Pro Arg Arg Cys
                85                  90                  95

Val Ile Pro Cys Gln Ser Phe Val Val Thr Asp Val Asp Tyr Phe Ser
                100                 105                 110

Phe Gln Pro Asp Arg Pro Leu Gly Thr Arg Leu Thr Val Thr Leu Thr
                115                 120                 125

Gln His Val Gln Pro Pro Glu Pro Arg Asp Leu Gln Ile Ser Thr Asp
 130                 135                 140

Gln Asp His Phe Leu Leu Thr Trp Ser Val Ala Leu Gly Ser Pro Gln
 145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
                180                 185                 190

Ser Gln Ala Thr Leu Gly Pro Glu His Leu Met Pro Ser Ser Thr Tyr
                195                 200                 205

Val Ala Arg Val Arg Thr Arg Leu Ala Pro Gly Ser Arg Leu Ser Gly
 210                 215                 220

Arg Pro Ser Lys Trp Ser Pro Glu Val Cys Trp Asp Ser Gln Pro Gly
 225                 230                 235                 240

Asp Glu Ala Gln Pro Gln Asn Leu Glu Cys Phe Phe Asp Gly Ala Ala
                245                 250                 255

Val Leu Ser Cys Ser Trp Glu Val Arg Lys Glu Val Ala Ser Ser Val
                260                 265                 270

Ser Phe Gly Leu Phe Tyr Lys Pro Ser Pro Asp Ala Gly Glu Glu Glu
                275                 280                 285

Cys Ser Pro Val Leu Arg Glu Gly Leu Gly Ser Leu His Thr Arg His
                290                 295                 300

His Cys Gln Ile Pro Val Pro Asp Pro Ala Thr His Gly Gln Tyr Ile
 305                 310                 315                 320

Val Ser Val Gln Pro Arg Arg Ala Glu Lys His Ile Lys Ser Ser Val
                325                 330                 335

Asn Ile Gln Met Ala Pro Pro Ser Leu Asn Val Thr Lys Asp Gly Asp
                340                 345                 350
```

```
Ser Tyr Ser Leu Arg Trp Glu Thr Met Lys Met Arg Tyr Glu His Ile
        355                 360                 365
Asp His Thr Phe Glu Ile Gln Tyr Arg Lys Asp Thr Ala Thr Trp Lys
        370                 375                 380
Asp Ser Lys Thr Glu Thr Leu Gln Asn Ala His Ser Met Ala Leu Pro
385                 390                 395                 400
Ala Leu Glu Pro Ser Thr Arg Tyr Trp Ala Arg Val Arg Val Arg Thr
            405                 410                 415
Ser Arg Thr Gly Tyr Asn Gly Ile Trp Ser Glu Trp Ser Glu Ala Arg
        420                 425                 430
Ser Trp Asp Thr Glu Ser Val Leu Pro Met Trp Val Leu Ala Leu Ile
        435                 440                 445
Val Ile Phe Leu Thr Ile Ala Val Leu Leu Ala Leu Arg Phe Cys Gly
    450                 455                 460
Ile Tyr Gly Tyr Arg Leu Arg Arg Lys Trp Glu Glu Lys Ile Pro Asn
465                 470                 475                 480
Pro Ser Lys Ser His Leu Phe Gln Asn Gly Ser Ala Glu Leu Trp Pro
            485                 490                 495
Pro Gly Ser Met Ser Ala Phe Thr Ser Gly Ser Pro Pro His Gln Gly
        500                 505                 510
Pro Trp Gly Ser Arg Phe Pro Glu Leu Glu Gly Val Phe Pro Val Gly
        515                 520                 525
Phe Gly Asp Ser Glu Val Ser Pro Leu Thr Ile Glu Asp Pro Lys His
    530                 535                 540
Val Cys Asp Pro Pro Ser Gly Pro Asp Thr Thr Pro Ala Ala Ser Asp
545                 550                 555                 560
Leu Pro Thr Glu Gln Pro Pro Ser Pro Gln Pro Gly Pro Pro Ala Ala
            565                 570                 575
Ser His Thr Pro Glu Pro Tyr Gln Thr Glu Met Arg Leu Val Val Leu
        580                 585                 590
Arg Thr Cys Val Gly Cys Leu Ser Pro Ala Val Ala Asp Ala His Asp
    595                 600                 605
Met Ile Leu Ile Trp Val Gln Arg Trp Glu Ala Pro Gly Gly His Pro
610                 615                 620
Trp Gly Leu Gly Leu Gly Arg Val Ala Gln Asp Trp Ala Arg Ser Val
625                 630                 635                 640
Arg Leu Arg Glu Phe Arg Leu Ala Ser Ile Val Thr Pro Arg Asn Gly
            645                 650                 655
His Gly Ile Gly Gly Arg Gly Gly Ala Arg Asp Ala His Glu Arg
        660                 665                 670
Leu Phe Gly Ser Phe Trp Gly Ala Leu Leu Val Val Ser Val Met Ser
        675                 680                 685
Val Gly Pro Pro Val Pro
    690
```

<210> SEQ ID NO 3
<211> LENGTH: 21968
<212> TYPE: DNA
<213> ORGANISM: Human
<220> FEATURE:
<221> NAME/KEY: misc_feature
<222> LOCATION: (1)...(21968)
<223> OTHER INFORMATION: n = A,T,C or G

<400> SEQUENCE: 3
tgactgtcga ccaattacat aacatcccac ccctgttttc tcatctacaa agtggagctt      60

-continued

```
ctagtggtaa cctatacata gatgtattca tatccgtaaa accttttgaa taatgcctgg      120
ctcatggaaa acactgcaat attgtcagcc actatcatga attctctctg tgtatgtgag      180
tactgtttgt gctctttgat gatattgatt tgttttaacc ttttaaagta aaagacacta     240
acctgtcctc cataattctg gttggtatgg tctatatgtt gaagtgcacc caagtttatg      300
ttgcaaccta agccccaatg tgagaatatc tggaggtagt gcctgtggca ccctataaaa      360
taccccagcg agctcccttg cttattccat gtgagattac agggagaaga ctgcaaggaa      420
caggccctca ccagatagtg aatctgcccg caccttgatc ttgaacttcc cagcctccag     480
aactatgaga ataaactttt gttactagta agccactcca tctatggtat gttgttacag     540
tagcctaacg gatgagtaca ttggtgcaaa gattttctgt ttgcactccg tccttttcctt    600 ttatggttca gtcagtttga caaattacag aagatttcac ttttatgtac ttctgccagc    660
ctttgtctct gtgatgtctc ctatgctttt aagcttaaag agttcaaagg cattcactcc     720
tctggtttgc agctttcata ggatgtaaca ttttacattt aaatttataa ttaacttgtt     780
atttggggaa tggtgtgaaa tggggtttta gataggcatt tttatgttgt taatcaatga    840
ttttagcatt ttttaaaatt taatatttca tcgcttcaca ttgattcctg attccttctc     900
agtctggggt caagtagagt ttgtttccag ccagcatgtc cattgataga ttctgtgtgt    960
gtgtatgtgt gtctgtgcat gtatctgtat gtgtgtgtgt atgtctgtgt gtaggtggta   1020
tatgcgagtg tgtatgtgtg tgtgtgttgt gcatgtatgt gtatgtgtgt ctgtgtatgt    1080
gtgcctctgt gtgtgaattt ctgtgtatgt gtgaatgtgt gtgcatgttt gtgtgtatat    1140
gtgtatatat gtgtatatac atgtatgtat ctgtgttgtt catgtgtgta tgtgtgcctg    1200
tgtctctgtg tgtgtgtttg tatgtgtgtg tgcatgtttg tgtgtgtata tgtgtgtata    1260
ttgtatgtat ctgtgtgtgt ctgtgtctgc ctctgtgtgt gtgtctgtgt gtgcatttgt    1320
gtgtatacat gtgggtatgt gtgtgcatgt tttgtgtgta cgtgtatata tgtatgtatc    1380
tgtgtgtgtc tgtgtgttgt gcgtgtgtgt gcctgcatgt gtccgtgtgc ttgtgtgtgt    1440
gtgtgtgttt gcgtgggcat cttgagtgaa gcttccaaca atctaacaga agaaaaggag    1500
ccacacttgt ctgttctgct ctcttgggta cttcccagac cagtgaaatg aaagggagga    1560 aaccccccggc ctccgaggag aaaagggaac tggcaagcag agggtggggg gatgacggta    1620
aaaggagcag gggtggggag agcacaggcc ctgtggaagt gaggacatgt gtgtgtacat    1680
gtgttcatgt ccagggggatg acactgtggc atccaacagc cgtggaccag cagcccacgg    1740
ggagcttagt aggagtcaaa tcctaggccc ccgtctcagc tgctctgctg tctagcgcat    1800
tgtgcagtgg taggtgtcag tgatccaagt ggggacccag tccctcaggc cacacagcgc    1860
atgtccattg ccttcatgcc gcaggagact gagggtcat gcatgagggc cacttctctg    1920
ggttgtcccc acaacactgg cggtgtccct gggacatgtg gaaagggggag gggcagctca    1980 ctgctgacat ctccttctgc aggcctggag gaggcagagg ccaggaggga gaggtcccaa    2040
gagcctgtga aatgggtctg gcctggctcc cagctgggca ggaacacagg acttcaggac    2100
actaaggacc ctgtcatgcc catggccagc acccaccagt gctggtgcct gcctgtccag    2160
agctgaccag ggtagatggt gctggcccag gggctgctct ccatgccct gctggccctg     2220 tgctgggagc gcagcctggc agggcagaa ggtgagtccc gtggctccca cccacttccc    2280
tgtccctgtc ctcactgctg cacctgggg gagggccgca gcgtatcctc aggatcctgc    2340
ccgccagccc tcctcctgct cccctccctc tgtctctccc cctggccttc cctgggcctc    2400
```

-continued

```
cccgcttcc ctcctcctgc acattcctgc tcatcctgtc ttggaaagtc cagctgagcg    2460
tgtctggctt ccttgcccac atttctcagg gcggcactcc cggcccctag gctccaggat    2520
ggctgctctg gccgtttccc tgcccctcct tccccagcag acactctctg tgcctcagtg    2580
gttcccacct ccgggacttt gctcctgcag ggccttggct ggggttctct ccctgcttca    2640
gccgctagca ccctccttgt gcctgaagcc cgcactggga tgctcctggg ctcttgaggt    2700
gaaatggccc ctcccaaggg ctcccagaga cctggcttct gtgataatgc tgggaccaca    2760
gtccccttaa caaataccag gctcctgagg acggggacta gagaggaggt gggaggttgc    2820
agggtagaac tctgccacgc tgcatcccag ggctgagtgt gtgccccctc ccaggctgca    2880
cagtcggtcc aggggccagg cctgtgcttg atgcatgtcc ctgtcctggg gtgggggggag   2940 gggaccgtgc ccaggaacag cacactgcgg aggcccagaa accatgctga gaaccaacag    3000
aatgtcttgc ttctgccagg agaggagggt ccgcaaccag gagcccaccc cggcagacat    3060
gaacacatgt acatgtgcct ggccacctgg tgcctctgca gggacctggg agaccccctcc   3120 ccagagcggg acatcccaaa gcagctgggg gtgatggtga caagggtccc tgcaggaaag    3180
agaggtgacc cccttctacc cctcttgtca gaaaccatcc cgctgcagac cctgcgctgc    3240
tacaacgact acaccagcca catcacctgc aggtgggcag acacccagga tgcccagcgg    3300
ctcgtcaacg tgaccctcat tcgccgggtg aatgagtgag tgatgctggg gcaggggcca    3360
cgggcnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnctcccca cccccttttgc ccaccgccgg   4260 ggcctgggcc tggaccaggg ctcctgtctg aggcctgaga cacgatgctg tctggtcctg    4320
ttgctcagga acatcacggc ccccaagtcc ccactctgcc ctgtgccacc caccatgccc    4380
tctcccagga tctttcccaa ttgccttgca aacctgcccc aaccccctct cagatgccca    4440
caggagtgca gcgcctgggc atctcctgac ctggcaaccc tgcggcccct ctttctctgc    4500
ttcctttgac agcagcattc cctaaagagt tgtccacatt caccacgtcc agtgtctttc    4560
cagccatttc ctcctgggcc cactccccta ggatgctgcc cccaccaggc cacccaaaact   4620 gctctggtcc aagtcagcaa atgtcccagg gagcaggatc tcatggttgg gcctccgcct    4680
tcttcctact tgaccagggg cagcccctga caaggaggac caccgcggcc tccctgcagt    4740
ttctcttgca cctgactctg cccacagctc acccagtgcc ccgggggccc tgcccatcct    4800
```

```
ctctttctcc ttgtctgctg cctcctgatg gcaagacacc caggcccagt ccatggacct    4860
cctctctgct gtatccactc tgcagagacc ccctcaggcc cctggggcat ctcccaaagg    4920
tgacctcaag cccacaattc ccctaagctc cagccctcca ggcgtactgg cctctccacc    4980
tgtcacttag acaacaggtg tctccgactc caaacgtcct caaccaaagt cccgctctca    5040
cccgagctgc gctgctgcct ctgtcttccc catctccctt tctaaatggg agctcctagt    5100
ggctcaaact aaacaacagg gaggattttg ttttgttttt aagtctcttt tgtcaccatt    5160
ccttcctgac tgctacatcc ctccaccagc aaatgctgcc aaccttatct caagcagaac    5220
atgaatctca cccacgccag cctgaccacc ctgttgcacg ccacttcctg tcacctgaat    5280
attccagaag cctcgtaact gggctccctg cttccaacat tgccacattc ccacctcagt    5340
ctattcgcaa ccgaggaccc tcaggaatcc tttcaaagca tttatcaaaa tctacaacac    5400
ctctgctcat gactgtttcc cactcactcg cagtgagatc caatcccatc atgtagatgg    5460
atgggtctcc tagacctccc tatcacacgc tctactccct gcgcactggt tttaggccaa    5520
gccacgcagc acaccaaact ctgcctgtcc cagggccttt gcacgtgctg ttcccatttc    5580
ctgaaatcct cacaatttgc acagtccctc cctcaatgcc tttaacattc tgccccagg     5640 tcacctcctt agagaagcct gcttgtccca tatttcaaat tgcctccctg gcccagccct    5700
tcctgcctcc tcacctgctt cttgctttat ttttccacat gaagttctct ccactgcaca    5760
cgctacacac tttgttccat gcaggtcccc ttctcccagg atggcagctc cgtgggcagg    5820 attttttgtgt gttttatcac tgctggcccc tgattctgaa cagagccagg catgtggtga    5880
gcactcgagc aacctttcgt gagtcagtga tacccataca ccctgggcta agccgtgtcc    5940
tctcccaaca gggacctcct ggagccagtg tcctgtgacc tcagtgatga catgccctgg    6000
tcagcctgcc cccatcccg ctgcgtgccc aggagatgtg tcattccctg ccagagtttt    6060
gtcgtcactg acgttgacta cttctcattc caaccagaca ggcctctggg cacccggctc    6120
accgtcactc tgacccagca tggtgagggg ctggggggccc tgcccggggc ttggtttcct    6180
gtgtggacag cgggggcacc aggggtggtc cagggagtct tcaaggcaga aggctgtggc    6240 ttgggggttgg gtgagggttt cttgagggat gagggtatgg tctggttaca tggagacttc    6300
agagcagagg ggcccctgac aaaggcttct cctgtgcccc tggctgctac cacctcccac    6360
taagccatgg gcttccagca ctgcaggctt gtcttgaaga aaaccgttct caccactcac    6420
ttagaaacct accaagttag aaaactctgt ccgcttagtt gtttcatctc atctctgaag    6480
caacccattt cctggatgtg gcccttgagg cccaggaggt cagatgcctc ctctgaagtc    6540
ccacagctga gcagtaatga cagagatggg gtcagccttc ccgggggctt cctgcatggt    6600
agacagggag cttgtctcct cgctgccctg gaggaggggc cccggtgtgg gccgaaatcc    6660
cacagtggtc catgaagcca tctgtggtct agggtggggt agatgattat tttatgtagt    6720
taggttttat ttgcctctat attagaaaga aatataacct gcacttcgaa gtcctggatt    6780
caaggaaatg gttgcttaga atgaagctaa acctgaaaag ggacacgttt tatgaaagtt    6840
ttcgttgacg tggcaaaaac ccatgctggt ggcaggctgg taggaggtac tgcaggctgt    6900
cattgggagt ctcagaacca cggcaggctt ggtgctgtta ttggtgcctt tggctgctgc    6960
tgaaacggag acagagggag gtgactagtc caaggcctct ctactgctgc tggcagagct    7020
gagatccagt gcaggatggt ctgagtcccc ggtcctaacc accgaaccac ctggtgctct    7080
ttgcaagggt cacacggaag gggctctgac catggcttcc tgccctttt tgccacaaca    7140
```

-continued

```
tcataaagcc actgccagag gagggatca gttaggccac caggagtcca tcagaagcaa      7200
catttccaca catgggtttg atggacacga gagtcccttc cttcccgaat ggagctcagg     7260
gggcccaggc tggagggagg ggaaacactg tatgccgtcc accgtgagaa cttactgaca     7320
gtggcgggtg ggtgcctcat gcaggggta aagggcaggg cccctgggag atcagaacag      7380
gcttcccaga gggaagagct ttgcaactca gatctgaagg gtagacagga ggggagggca     7440
gtaagagcct ctctggcagg gtaacagctg tgcagaggct gggggatcag aagggcatgg    7500
gcagctgggg aacctgctca ccattgtgtc caggagcat cagcttcaag ggctggacag      7560
cggtgggaag aagcaggaga cacaggtaag gacctgtccc tggagaggct tctgtctcct    7620
gcagtctcag gtagagggga ccctctaggc atggagagca ctgaggggaa atgacatgat    7680
cagatgtgga tgtgagaatg ctggggacag gggacttaca gggtagattg gaggagcatt    7740
agttgggaaa gaagttgaaa ttcaggctgt ggcctaaagc actcattcct agaaatgatg    7800
aggacacaac tggctaggag atggggacat gagggcatgc aaatcatagt tcagatatac    7860
acacaattca ttcattcaac cttctttcct tgagcgccta cataagccaa cgaagcagtc    7920
aacaaaccag ccagcaaccc tgcccttgga gcttacagcc tggaaacaag gaaggtttct    7980
aaggcgatgg agacaactta gatataggga gagaagtgtg gcccttggcc tcctggagcc    8040
tgtgttgagt agcgaggtag ggtccagcct aatgcagatt agcaatgaat caaggatgct    8100
gggaggtact gggcaggcga caggcatgca tctgatctgc tctgagtctc catgtttgga    8160
gaccttggac attttacttc ctctatgagt ttctccgtct gtgaaatgag ctggtggact    8220
caagaggttt ctcttgagtt ggctgagcag gtttctgatg gggctcccag tctgcgcagt    8280
ttgtggcagc ttccgagagg gctctgccgg gaagagctcc ccctccatga cagcctcggg    8340
ggctgggagt gcagtgaccc atgagggacg cctgtcctgg ctgtgggtga ggaggggcgg    8400
ttcccctgct gtgtgtctgc cgttctgggt tgatggttcc tgacatgctc tagcatgcca    8460
taacccatgt ccagcagaga gcacttacat cctatgtgtg aggatgtttt cgtttgaaag    8520
ccatccctca gcaagcagac accagaaacc agaaatcagg tgccgtgtct tcattctgca    8580
ttttcttgaa caacccagag ttcccaggag atagatgctt gccttgtggc tgcaaggatt    8640
tcatgagaag ccccaaagtt gcttacgcgt atttgttcat tcattcactc attcaccttg    8700
ccccataatt cactgagaag ccgcatctca gcctggaggt agggaagggg gtcaggacca    8760
atcccaccca cccccatctc ctcacacctt aggggaggca gacacagaag cataggaatc    8820
cctcagctgt ggtaaggccc tggtggaggg aattccactg agctatggtg aaatgagaga    8880
aggaatgagg gattccgcct ggagatgcag atccgaggat gttcctagag ccggaggcat    8940
ttgcccgggg cactgacaac aggaaggacc ctgggcagga ggaagggagc ttggacagca    9000
ggagggggga ggccgctgaa ccgcaggccc ctctgctagc aggagccacc caggccgcag    9060
cgtgggcagt ggggagcctc aggacagagg aggctccaat gagtttcctc gccagcgctt    9120
tttatggagt tcgggtcacg tgcgcattgc aatctgcacg gctttccatt gctttcatgt    9180
tgaaacccta cagttttgca gatgaagggc tgaggctcac agaggagacg ggtcttgctc    9240
aaggtccctc agctgctggg ggcaggggtg gcctggaacc ccctgtgtcc acacaaaagg    9300
ccatgcaggc cctgactgcc ccccagcggt ccagcccta ggtgcccttc acttcctccc     9360
ctccagtcca gcctcctgag cccagggacc tgcagatcag caccgaccag gaccacttcc    9420
tgctgacctg gagtgtggcc cttggagtc cccagagcca ctggttgtcc ccaggggatc     9480
tggagtttga ggtggtctac aagcggcttc aggactcttg ggaggtagga accacggcca    9540
```

-continued

```
gctctgcccc agcccgaagg gatgggcagc acccctcctc cagcacccac tgtctcctga    9600
caggacgcag ccatcctcct ctccaacacc tcccaggcca ccctgggggcc agagcacctc   9660 atgcccagca gcacctacgt ggcccgagta cggacccgcc tggccccagg ttctcggctc    9720
tcaggacgtc ccagcaagtg gagcccagag gtttgctggg actcccagcc aggtaatgtt    9780
gccagagccc aggaaatgcc ccgtggtggg agggcaggct catcaggagc tcctggcaca    9840
gcagggttcc tgggctccac ctgggggctt cccagatctc ctgctgccat ctttccagta    9900
gcgtccctgg gccgtcccac ctctactgtg accactgacc agtaggactc tgcatctgtt    9960
cactttgggt ttccagtttt ctgcacgttc tctgccaatg gcaattacaa taataacaac   10020
aacagtgcta ttagcagctg tgtgttaatg gaggctacag gatgctcagg gcttacccac   10080
atttttcagt tcaatcccca aacactgaaa cttagatact atttccattc tcccgggagg   10140
gcgtgcaggt gcacagaact ctctctctct ctctcggagc tgttggacac acagctggca   10200
ggttcaggct gaagtttcag ccctggtctt ttggccccag agctcatgac ctctgtgtga   10260
tgaatcacac ggtgggcacc cactgagagc tatgggaggg atgaatgacg gagtacatga   10320
ggacctgtct ccaacccagg ggatgaggcc cagccccaga acctggagtg cttcttttgac  10380 ggggccgccg tgctcagctg ctcctgggag gtgaggaagg aggtggccag ctcggtctcc    10440
tttggcctat tctacaagcc cagcccagat gcagggtgag catctttttt ctccatcccc    10500
tcccctcctc ttggccttgc tctctccaag cttcctcctg tcctgggggc cccagcagaa    10560
gccacagccc accctaagct ctcctccctc ccgtgtgccc tccctctccc tgccctcagc    10620
tctgctgtgc cctcaggga ggaagagtgc tccccagtgc tgagggaggg gctcggcagc    10680
ctccacacca ggcaccactg ccagattccc gtgcccgacc ccgcgaccca cggccaatac   10740
atcgtctctg ttcagccaag gagggcagag aaacacataa agagctcagt gaacagtgag   10800
tttgctccta gcccgctgtg gggatggtct gggaccagca ccctcatt gtgtaacccg      10860 aatcagttca gggttcctcc tggccccgt ttcatgtttg tcactttcaa agagatgcag     10920
tccagtgacc aaaagtgaac agagaagcaa tgaaccacg acggcagtgg ccaaaaacag   10980
gagcagatct ttaaaacctc tgatctcttg tcctttctt ctgcttccct ctcccatcct    11040
gcagctctct aaatctccac tgctagccac accctcctgg tcctgtcacc aaaaccttcc   11100 cttcattcc tcattggat ttcctctttc tgatatccga aattccccac cgactgatat     11160 tctatctta atgtaattga tctatgatgt acttttcaac tggagcctgt ggtgtgtaca    11220
aatagtgttg atccttggag gttaacatcc ctcgtttctg tgatgtaaca aggaccccag   11280
tgcaatggaa cctctcacgt tgtttcatga tgaccaagtt cttccatcca gtctttagca   11340
tatgtgaagg gcagaggcca atttgtctta attacctggg tttgaattta ccattaactc   11400
tcttgggatc ctcactggaa aaaggaattc tgattgttca aaagcacagg atatattaag   11460
ggcctcatat aatgcctggc acataagaga cctcagcaaa ttacgggcat tcatattatg   11520
tttatacagt gaaggcatca aggttataag cattctcttt tttcttttgg gtagactgaa   11580
gctcagagag gttgagtggc ttacttaaag ctgcacagct attagtaggc agatcaagat   11640
tagagttcag aacttctcac tccctgccca gtttctgctt tctttaccct ttgcctcttt    11700
caagttgtgg gtctgccggc caggtgggag gtgctgtctg caaagggctt ccctttctct   11760
ttggccacta tctggctggg gagaggcctc acctagatgt tgttgaaggc ctgttacagc   11820
cgctttattg gggattttct ggcgatgaga acgtgtgaat gtcctggcct ttagtcaact   11880
```

-continued

```
ccctacacct ctgagagtgt cagacaagag agcccatcac actggtggga ttgcaatctt   11940
tgcctctacc actgcttagc tgcctttcct tagggcaagt tacttaatgg ttctgtgact   12000
cagtttccct gtttgtgaaa agtgaaggtt aatagtaccc accatatagg gctgttagaa   12060
tggagtggaa taattcatgt agaataagta tgtataacag tggctaaaac atagtcaggc   12120
tgggcgcggt ggctcacgcc tgtaatccca gcactttggg aggccaaggc atgtggatca   12180
cgtgaggtca ggagctcaag accagcctgg ccaacatggt gaaacccgt ctccactgaa    12240
aatacaaaaa ttagctgggc ttggtggcgg gtgcctgtaa tcccagctac tcgggaggct   12300
gaggcaggag aatcacttga acccaggagg cagaggttgc agttagccaa gatcacacca   12360
ctgcactcca gcctgggcaa cagagtgaga ctccgtctca aaaaaaaaaa aaaaaaaat    12420
agccagttgc ctagaataga accaactaac agtggtttta tttttactgc aaaaaataaa   12480
aataaaaata ggagtagtgc aagcactggg ccacatcact acaaaacaag tgtatctcag   12540
catctcccac gagaatacca ctcaggtcaa acatgatat agtgaagtgg ggatgaaaag    12600
gatccaacca tgggcagaac ctggggtctg gtgccagtgg agacagcccc agtgtctagc   12660
atgagacacg gggaatgttc cgttggaggg tgggtatgat gactctcctg aaagcttccc   12720
tccctccagt ccagatggcc cctccatccc tcaacgtgac caaggatgga gacagctaca   12780
gcctgcgctg ggaaacaatg aaaatgcgat acgaacacat agaccacaca tttgagatcc   12840
agtacaggaa agacacggcc acgtggaagg tgagggcctt tgcccaggga cgggagaaac   12900
actgggagg gcgggagaag ggaaagcaac cagaggcatt ccacctgcaa ggcgtcgggc    12960
ccttggcagg tgaccagtga gaggtagcca ctgggacgtg gtgatcacta ggctgtgtgg   13020
tcagcaggtc actgtcctgt ctcttggtga agtaactgag gtttgaaaa gtggcgtggc    13080
ttggccaacg tgaacagctg accctgagtc cccaggcaac agaagaccct ctgggcaggg   13140
aggggttgaa aggccactgg gaagaaggtt ttcaaaagtc atgaaagttt ggggttattt   13200
cctcagagga atctcatctg gacacacatg gaggctcaga cagagctgct tctaatgagt   13260
cgggggtgcg cccaggccag ggctcggtcc cctgcctcca cagagcccag aacagaaacc   13320
acagaaccaa ccccacacct tcagtctaga aatgggcaa ctgaggctag gagggaggtg    13380
ggccagtggt ggagccagga gcgggccctg gggtcctgaa cccccattct cagggtccag   13440
agtccagtcg gcctgcactg cgttcctgaa aaggccacaa tatgggtgca agctgcccca   13500
gaagggctgg gagctgagaa ggctcaaaat agggtgggac aggtggcttc agggttctgg   13560
gcctcagtgt tgtcaatgtc aggggctgca ctgacaggcg gagtccccgg tgccatccga   13620
agtgctgtcc gtgggtgggc cctcaggag gatccacggt ggtgagagag aagccgcagc    13680
aggcctgggg tatggcagga gctaggagcc agcgaagccg agggtccagg tgggagggat   13740
ttgcagctgc tcccacgggc accgggccag gcctcaccct cagtgccaac ccacaggaca   13800
gcaagaccga gaccctccag aacgcccaca gcatggccct gccagccctg gagccctcca   13860
ccaggtactg ggccagggtg aggtcagga cctcccgcac cggctacaac gggatctgga    13920
gtgagtggag tgaggcgcgc tcctgggaca ccgagtcggg taggtgaagg ctggagtcca   13980
gagcttctgg ccaggaccag ctcatagttt ctcactgcca gaaatccccc aatgcagcag   14040
ccgtagcagg cctgcaacaa cttgtaggtg agccgtctcc ccgattagat ggtggccaaa   14100
gagaaaggga aggcctttgc agagagcacc tcccacctgg tcatcagacc cgcaagttga   14160
aagaggcaaa gggtaaagca ggcagaaact gggcgtggag tcagaagttc tccacccact   14220
cttcatgaga cagcacagct gggcagagga tgccacatct ctgggtgggc acagagatgt   14280
```

```
ggggctccag accccactcc actcaggcct ccttccctcc cttggaccac tagtcgttgg   14340
aaagtgacac ctggtgttca gtacagactg caagtgagga cttgagggag cagaggagag   14400
caggtctcat gatcgctcct cctttaaact gggacttagg cttctgttaa tatggccctt   14460
ggtttcttag cttttgggac taccaagttt ttgtggttgc tcagcccgag tttcctgtta   14520
ccatggaagc aagaaaatct agagccacag actgggtcct tggattggaa ggttttgctg   14580
tgattccttc atcttcccac ctccctgcac ttgctgcgtg cactgacccc tcacctttca   14640
ccatagtgac caccaggcga ctcccgcaga acaagacaag tccaaggggt ggtttcagag   14700
agagtaagga tacaggagat attgggagca acccaagtcc ccagccaggc ttggtagcgg   14760
cagggcccca gggagagggc cacaaccagg tagaaaggag gccggaccaa tgggcccaag   14820
agaggaggaa gagggagtc ctggaggaac ctggcctggg agctcagggc tgggcagcag   14880
gtgggatcag gggcctctgg aggggccttt gctcctgctg gtgcctctgc cactatgcct   14940
ttccccatct ccacctctaa tccttcctat tactggaggc cagctaata tgccacctcc   15000 ttcaggaagt cccctgtgat tgccatgaac agtggttctt gccctccctg tagcacctcc   15060
tgtgctatag atcctggaaa ggatctgacc ctcctgtgtc ctcccagcac tttgaacact   15120 gtggggttc agaccaatgc ccttcccagc atggatctgg cctctctccc ctaatcccc   15180 aaggcagtaa gttccagagc cctgggcctg cacagagcgg ggtcttaagg aatactgcac   15240
caaccccact ccctgccctg aggtcgattt cccgcccaga tgctgacatt cctctttctc   15300
cccggctgct ggaagtgctg cctatgtggg tgctggccct catcgtgatc ttcctcacca   15360
tcgctgtgct cctggccctc cgcttctgtg gcatctacgg gtacaggtga ggggactctg   15420 tgggctgga ggtggcagcc gagacccag agggcactgg ggaatcccac ccagctccct   15480
ccaggccctg ctctgccgct cccttcctgg gcctcagttt ccctctgggg catgagcatg   15540
ggagcagctg gccatgaggt tctctgatgc tgtcacctcc cgtggtgtct tccaggctgc   15600
gcagaaagtg ggaggagaag atccccaacc ccagcaagag ccacctgttc caggtaggaa   15660
ctggctgcga ggggcggagt gggggcttct ctgttcctgc ctctcttgtc tctgtcccca   15720
cctccctcct tcccttcctg tgggctttgg gtggtaggga tgtaggtgga ctgggctttg   15780
ggagctttgg gagtgggcc agcacttgga aattcattcc cgggattccc tggagtgccc   15840
acacctggcc ctgcctgcca gagctctgca tggagcccag tggagagaac tgagtgtggg   15900
gatgcctggg acagggtggg ctcacagagg gggttcctgc taccaggatg gatgggtgt   15960 caggaggcag aagggctccc caaggacaag atacctgggc tgagctttga gggtcccagt   16020
ggtgccaggt ggcaaaagtt gctctggctc agggcatctt gaggtggag acagaaaccc   16080 ttcaggaagg gagctgaagg ggtgggacag gaggctgggg ccatgttgg gaggctgaga   16140 tgaccatggg gaagacacca gcgtgtgggt gatgggagcc ctatagtcag gcaggcaggg   16200
ccagctttgc ctgtggaggg gtctcttggc tggtgtggag gagaaatggg ggtgagcatg   16260
gagacaggca ctccaggtta gaaaaatcac aggaaaaggg ccctgtcctc aggtagcagg   16320
gacatggggg aagtccccgc ccctctctgg gcctcacttt gctggtgtca aaggccgtg   16380 gccagtcctg aagaagtgga gattcttctc ttgtctgggg gctccttgaa tcctcctgca   16440 ccccgtcac cctctgcctt gcccccacct cggacctcct gatgctcacc ggcccaaatg   16500
tctctgctct tgcagaacgg gagcgcagag ctttggcccc caggcagcat gtcggccttc   16560
actagcggga gtcccccaca ccaggggccg tggggcagcc gcttccctga gctggagggg   16620
```

-continued

| | | | | | |
|---|---|---|---|---|---|
| tgagtgggct | cgtggatcac | tcctgacctt | tggggttcat | acgggggct | gactccattg | 16680 |
| tggaaatcag | ggactcaagt | gaggctgcct | gtggctcact | gtgaagggat | ccaagggagc | 16740 |
| tggtttgcac | taaagcagga | ggcacctggg | gggatgtga | ggaagaactt | cctctttcca | 16800 |
| ggtaaggaag | tgccagacaa | ggggagtgac | cggaagtgaa | agagggaaac | agttggcctt | 16860 |
| cccctccctg | gctgcctcag | aggcgtcaca | ctgcagaggc | ctcatggggt | agctgggggct | 16920 |
| gcagactccc | gggaactcgg | cgcctgagcc | ggcagctgac | caccaactcg | gcagggagaa | 16980 |
| gggggtggca | tggttgatag | aatgatgaa | ggttgccca | gtgcacaggc | tgggcatgag | 17040 |
| cctggtgctg | aaggaggatg | gactttaagg | tcaaaggga | gagggtacca | gccttgcaga | 17100 |
| ggaagacctt | gagctcagca | tggaggatgg | agctcctgag | ccacggaaag | actgaatcca | 17160 |
| tgtcccatgt | ccttctctgg | ggcccctgct | ccctcaaccc | tgtcccgttc | aggttctctc | 17220 |
| tgtgagatct | ggggacatc | agggcttcca | gagaaccatc | tccacccccac | caagaccctt | 17280 |
| gtgcctgacc | cggatcatct | gcccaggtg | gtcccaactc | ttctgcccat | tttcttccca | 17340 |
| cagggtgttc | cctgtaggat | tcggggacag | cgaggtgtca | cctctcacca | tagaggaccc | 17400 |
| caagcatgtc | tgtgatccac | catctgggcc | tgacacgact | ccagctgcct | cagatctacc | 17460 |
| cacagagcag | cccccagcc | cccagccagg | cccgcctgcc | gcctcccaca | cacctgagaa | 17520 |
| acaggcttcc | agctttgact | tcaatgggcc | ctacctgggg | ccgccccaca | gccgctccct | 17580 |
| acctgacatc | ctgggccagc | cggagccccc | acaggaggt | gggagccaga | agtccccacc | 17640 |
| tccagggtcc | ctgagtacc | tgtgtctgcc | tgctggggg | caggtgcaac | tggtccctct | 17700 |
| ggcccaggcg | atgggaccgg | gacaggccgt | ggaagtggag | agaaggccga | gccaggggc | 17760 |
| tgcagggagt | ccctccctgg | agtccggggg | aggccctgcc | cctcctgctc | ttgggccaag | 17820 |
| ggtgggagga | caggaccaaa | aggacagccc | tgtggctata | cccatgagct | ctggggacac | 17880 |
| tgaggaccct | ggagtggcct | ctggttatgt | ctcctctgca | gacctggtat | tcaccccaaa | 17940 |
| ctcaggggcc | tcgtctgtct | ccctagttcc | ctctctgggc | ctcccctcag | accagacccc | 18000 |
| cagcttatgt | cctgggctgg | ccagtggacc | ccctggagcc | ccaggccctg | tgaagtcagg | 18060 |
| gtttgagggc | tatgtggagc | tccctccaat | tgagggccgg | tcccccaggt | caccaaggaa | 18120 |
| caatcctgtc | cccctgagg | ccaaaagccc | tgtcctgaac | ccaggggaac | gcccggcaga | 18180 |
| tgtgtcccca | acatccccac | agcccgaggg | cctccttgtc | ctgcagcaag | tgggcgacta | 18240 |
| ttgcttcctc | cccggcctgg | ggcccggcc | tctctcgctc | cggagtaaac | cttcttcccc | 18300 |
| gggacccggt | cctgagatca | agaacctaga | ccaggctttt | caagtcaaga | agcccccagg | 18360 |
| ccaggctgtg | cccaggtgc | ccgtcattca | gctcttcaaa | gccctgaagc | agcaggacta | 18420 |
| cctgtctctg | ccccctggg | aggtcaacaa | gcctggggag | gtgtgttgag | accccaggc | 18480 |
| ctagacaggc | aagggatgg | agagggcttg | ccttccctcc | cgcctgacct | tcctcagtca | 18540 |
| tttctgcaaa | gccaaggggc | agcctcctgt | caaggtagct | agaggcctgg | gaaaggagat | 18600 |
| agccttgctc | cggcccccctt | gaccttcagc | aaatcacttc | tctccctgcg | ctcacacaga | 18660 |
| cacacacaca | cacacgtaca | tgcacacatt | tttcctgtca | ggttaactta | tttgtaggtt | 18720 |
| ctgcattatt | agaactttct | agatatactc | attccatctc | ccctcattt | ttttaatcag | 18780 |
| gtttccttgc | ttttgccatt | ttcttccctt | ctttttttcac | tgatttatta | tgagagtggg | 18840 |
| gctgaggtct | gagctgagcc | ttatcagact | gagatgcagc | tggttgtgtt | gaggacttgt | 18900 |
| gtgggctgcc | tgtccccggc | agtcgctgat | gcacatgaca | tgattctcat | ctgggtgcag | 18960 |
| aggtgggagg | caccaggtgg | gcacccgtgg | gggttagggc | ttggaagagt | ggcacaggac | 19020 |

```
tgggcacgct cagtgaggct cagggaattc agactagcct cgattgtcac tccgagaaat   19080
gggcatggta ttgggggtcg ggggggcggt gcaagggacg cacatgagag actgtttggg   19140
agcttctggg gagccctgct agttgtctca gtgatgtctg tgggacctcc agtcccttga   19200
gaccccacgt catgtagaga agttaacggc ccaagtggtg ggcaggctgg tgggacctgg   19260
ggaacatcag gagaggagtc cagagcccac gtctactgcg aaaagtcag gggaaactgc    19320 caaacaaagg aaaatgcccc aaaggcatat atgctttagg gcctttggtc caaatggccc   19380
gggtggccac tcttccagat agaccaggca actctccctc ccaccggcca cagatgaggg   19440
gctgctgatc tatgcctggg cctgcaccag ggattatggt tcttttaaat ctttgccttt   19500
cagatacagg aaaaataatg gcattaaatt gctttaattt gcattatttt agttatccag   19560
tttgcacata tttttatagg tatcttaggc atcgattggt attttttaac tgggccaagc   19620
ccattaaggt ctttcttctg ttgggtgcta tcatttttcct gattaagtct ttttgactat   19680
tgacatacag tctttcacag atggtggagt gttttttcccc caaatctgtt gtttgtctta   19740
taatgttgta tatgaggttt tatggtgtat gaatatgaat gcttctgtaa tgtcaaacag   19800
atccctagta aactccttct tcacttttac tgtcagattt acaaaggtcc tcccattgca   19860
aagcagtgtt tgtcctaatt tatatattgt ttttctagtt cattttgtgt ttccaacttt   19920
tcatgtaaaa ttttaattat ttttgaatgt gtggatgtga gactgaggtg cctttggta    19980 ctgaaattct ttttccatgt acctgaagtg ttacttttgt gatataggaa atccttgtat   20040
atatacttta ttggtcccta ggcttcctat tttgttacct tgctttctct atggcatcca   20100
ccattttgat tgttctactt ttatgatatg ttttcataag tggttaagca agtattctcg   20160
ttacttttgc tcttaaatcc ctattcatta cagcaatgtt ggtggtcaaa gaaaatgata   20220
aacaacttga atgttcaatg gtcctgaaat acataacaac attttagtac attgtaaagt   20280
agaatcctct gttcataatg aacaagatga accaatgtgg attagaaaga agtccgagat   20340
attaattcca aaatatccag acattgttaa agggaaaaaa ttgcaataaa atatttgtaa   20400
cataaaacaa agtgaaaccc tgaatttgtg tgtgcatgtt ggtgtagttg gaggaagggg   20460
ttgctctttg aaacctcaat tgctattgta agtgatacag ctccagtgac tggaggaaca   20520
ccagggtcct tagtcttgcg ccgatttaaa taaaacgaca cggaaacaca tggagtggtt   20580
ttaaggagtg gagagtttaa taggcaagaa agaaggaaga agctcccctg tacagagaca   20640
gagggagggg ggatccaaag ctgagagagg aaaccctgag tgccacagaa ataagccagt   20700
tatatgagga ggctagagaa ggcagtatct gatttgcata gggctcaggg gattggtttg   20760
accaggcatg tcattcatgt aaccctgaa aaacctggcc ctttcaccct agcattttaa    20820
tatgcaaatg cagggcgcca tgatgttcta cacaggtggg actatgtggg ggtggccata   20880
ttgccaggca aacatgggga caaggaaaag atggcgggaa tccccatgtt tgggtggacc   20940
cagtttctaa cggtctgcat ttgcatatca aaggttgcca gcctgattct aagagccggg   21000
gctttcctgc tagacaagaa acgttttttg gagctgcttt taaacagaa cgaaaaactt    21060 cccaaggacc acttttcctc tttatctgcc tcaaataatt ttttaataat tcctataaca   21120
caaggaaatg aattctgcca aacagaaggg cctttggtct ttggggcact acagtgggta   21180
catgatggcg tgtggaacac cacgcaatgg agggagacgc agggcactcc tgggaaaatc   21240
caggagggat gagggaagag gaaagacagt gagggaaagg aggataaaga acacacttt    21300 aaaaaatcgt tcattattat ctgaaattcc aacacaactg aacgtcctgt attttccct    21360
```

-continued

```
agtcatgaga gtgaaaaact aaatagagac tgagttcccc atacaaataa ctgagagtga   21420
tcgagagctt attcctggca ggccccattc gagtgacctc taagatcaat tcatttagat   21480
actatggaag tggaagatac tatctttatc atttttgtca ttgaggaaac taaggcacag   21540
agatgtcata caacttgccc caggtctgcc agcaggtaag gggcagagcc aagatttgaa   21600
ctgtagccct gtgtctcaga gcctgccctc aaaaggtaag tctctcacct aaagatccat   21660
acggagatgt aagatgatcc atgttggttg gcaagacgga aaaatccata accaaataa    21720 attgatttgg tggcagggggg agattgaatc agaggtgacc ctgaaaagtg tctgtttatc   21780
tgggagctga acactgaagg tgcaattctc acccattgga gtccagagag accttccctg   21840
gaggactgca gctccctcat ctgtcttccc ctgagaaccc agcccagagc catgcatgta   21900
gtaggtgatc attgaggtga gcaaggcctg caggaggctg tccctaagat ggaggagaac   21960
aaaaaact                                                            21968
```

<210> SEQ ID NO 4
<211> LENGTH: 581
<212> TYPE: PRT
<213> ORGANISM: Human

<400> SEQUENCE: 4

```
Met Val Leu Ala Gln Gly Leu Leu Ser Met Ala Leu Leu Ala Leu Cys
  1               5                  10                  15

Trp Glu Arg Ser Leu Ala Gly Ala Glu Glu Thr Ile Pro Leu Gln Thr
                 20                  25                  30

Leu Arg Cys Tyr Asn Asp Tyr Thr Ser His Ile Thr Cys Arg Trp Ala
             35                  40                  45

Asp Thr Gln Asp Ala Gln Arg Leu Val Asn Val Thr Leu Ile Arg Arg
         50                  55                  60

Val Asn Glu Asp Leu Leu Glu Pro Val Ser Cys Asp Leu Ser Asp Asp
     65                  70                  75                  80

Met Pro Trp Ser Ala Cys Pro His Pro Arg Cys Val Pro Arg Arg Cys
                 85                  90                  95

Val Ile Pro Cys Gln Ser Phe Val Val Thr Asp Val Asp Tyr Phe Ser
            100                 105                 110

Phe Gln Pro Asp Arg Pro Leu Gly Thr Arg Leu Thr Val Thr Leu Thr
        115                 120                 125

Gln His Val Gln Pro Pro Glu Pro Arg Asp Leu Gln Ile Ser Thr Asp
    130                 135                 140

Gln Asp His Phe Leu Leu Thr Trp Ser Val Ala Leu Gly Ser Pro Gln
145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
            180                 185                 190

Ser Gln Ala Thr Leu Gly Pro Glu His Leu Met Pro Ser Ser Thr Tyr
        195                 200                 205

Val Ala Arg Val Arg Thr Arg Leu Ala Pro Gly Ser Arg Leu Ser Gly
    210                 215                 220

Arg Pro Ser Lys Trp Ser Pro Glu Val Cys Trp Asp Ser Gln Pro Gly
225                 230                 235                 240

Asp Glu Ala Gln Pro Gln Asn Leu Glu Cys Phe Phe Asp Gly Ala Ala
                245                 250                 255

Val Leu Ser Cys Ser Trp Glu Val Arg Lys Glu Val Ala Ser Ser Val
```

-continued

```
                    260                 265                 270
Ser Phe Gly Leu Phe Tyr Lys Pro Ser Pro Asp Ala Gly Glu Glu Glu
            275                 280                 285

Cys Ser Pro Val Leu Arg Glu Gly Leu Gly Ser Leu His Thr Arg His
        290                 295                 300

His Cys Gln Ile Pro Val Pro Asp Pro Ala Thr His Gly Gln Tyr Ile
305                 310                 315                 320

Val Ser Val Gln Pro Arg Arg Ala Glu Lys His Ile Lys Ser Ser Val
                325                 330                 335

Asn Ile Gln Met Ala Pro Pro Ser Leu Asn Val Thr Lys Asp Gly Asp
            340                 345                 350

Ser Tyr Ser Leu Arg Trp Glu Thr Met Lys Met Arg Tyr Glu His Ile
        355                 360                 365

Asp His Thr Phe Glu Ile Gln Tyr Arg Lys Asp Thr Ala Thr Trp Lys
    370                 375                 380

Asp Ser Lys Thr Glu Thr Leu Gln Asn Ala His Ser Met Ala Leu Pro
385                 390                 395                 400

Ala Leu Glu Pro Ser Thr Arg Tyr Trp Ala Arg Val Arg Val Arg Thr
                405                 410                 415

Ser Arg Thr Gly Tyr Asn Gly Ile Trp Ser Glu Trp Ser Glu Ala Arg
            420                 425                 430

Ser Trp Asp Thr Glu Ser Val Leu Pro Met Trp Val Leu Ala Leu Ile
        435                 440                 445

Val Ile Phe Leu Thr Ile Ala Val Leu Leu Ala Leu Arg Phe Cys Gly
    450                 455                 460

Ile Tyr Gly Tyr Arg Leu Arg Arg Lys Trp Glu Glu Lys Ile Pro Asn
465                 470                 475                 480

Pro Ser Lys Ser His Leu Phe Gln Asn Gly Ser Ala Glu Leu Trp Pro
                485                 490                 495

Pro Gly Ser Met Ser Ala Phe Thr Ser Gly Ser Pro His Gln Gly
            500                 505                 510

Pro Trp Gly Ser Arg Phe Pro Glu Leu Glu Gly Val Phe Pro Val Gly
        515                 520                 525

Phe Gly Asp Ser Glu Val Ser Pro Leu Thr Ile Glu Asp Pro Lys His
    530                 535                 540

Val Cys Asp Pro Pro Ser Gly Pro Asp Thr Thr Pro Ala Ala Ser Asp
545                 550                 555                 560

Leu Pro Thr Glu Gln Pro Pro Ser Pro Gln Pro Gly Pro Pro Ala Ala
                565                 570                 575

Ser His Thr Pro Glu
            580
```

ISOLATED HUMAN RECEPTOR PROTEINS, NUCLEIC ACID MOLECULES ENCODING HUMAN RECEPTOR PROTEINS, AND USES THEREOF

FIELD OF THE INVENTION

The present invention is in the field of receptor proteins that are related to the cytokine receptor subfamily, recombinant DNA molecules, and protein production. The present invention specifically provides novel receptor peptides and proteins and nucleic acid molecules encoding such peptide and protein molecules, all of which are useful in the development of human therapeutics and diagnostic compositions and methods.

BACKGROUND OF THE INVENTION

Receptor Proteins

Many receptor proteins serve as targets for the action of pharmaceutically active compounds. Additionally, many phamaceutical/therapeutic agents act by competing with and/or blocking the binding of the receptor with it's natural ligand. It is, therefore, important in developing new pharmaceutical compounds to identify receptor proteins that can be put into high-throughput screening formats. The present invention advances the state of the art by providing novel human receptor proteins that can serve as drug targets.

Cytokine Receptors

The novel human protein, and encoding gene, provided by the present invention is related to the family of cytokine receptors, particularly the hematopoietic and inflammatory cytokines, and shows the greatest degree of similarity to granulocyte-macrophage colony-stimulating factor 2 receptor, beta chain (GM-CSF2RB); this beta chain is also shared with the interleukin-5 (IL5RB) (Tavernier et al., *Cell* 66: 1175–1184, 1991) and interleukin-3 receptors (IL3RB) (Kitamura et al., *Cell* 66: 1165–1174, 1991). Thus, references herein to CSF2RB include GM-CSF2B, IL5RB, and IL3RB.

Mutations in CSF2RB are associated with pulmonary alveolar proteinosis (Dirksen et al., *J. Clin. Invest.* 100: 2211–2217, 1997) and acute myeloid leukemia (Dirksen et al., *Blood* 92: 1097–1103, 1998). Mutations in CSF2RB may also lead to cancer (D'Andrea et al., *Blood* 83: 2802–2808, 1994) and mutations that lead to over-active CSF2RB may cause hematopoietic disorders, neurological disorders, and myeloproliferative disorders such as polycythema vera (D'Andrea et al, *J. Clin. Invest.* 102: 1951–1960, 1998). Furthermore, CSF2RB-mediated cytokine signaling plays an important role in regulating cell fate decisions and it has been suggested that a key step in lymphoid commitment is down-regulation of the cytokine receptors that modulate myeloid cell development (Kondo et al., *Nature* 407: 383–386, 2000).

For further information regarding cytokine receptors such as CSF2RB, see Hayashida et al., *Proc Natl Acad Sci U S A* December 1990;87(24):9655–9; Tu et al., *Blood* Aug. 1, 2000;96(3):794–9; Herman et al., *J Biol Chem* Mar. 3, 2000;275(9):6295–301; Sayani et al., *Blood* Jan. 15, 2000;95(2):461–9; Gorman et al., *J. Biol. Chem.* 267: 15842–15848, 1992; Jenkins et al, *EMBO J.* 14: 4276–4287, 1995; Robb et al., *Proc. Nat. Acad Sci.* 92: 9565–9569, 1995; and Shen et al., *Cytogenet. Cell Genet.* 61: 175–177, 1992.

Due to their importance in hematopoietic, inflammatory, and neurological disorders, as well as cancer, leukemia, and myeloproliferative disorders, novel human cytokine receptor proteins/genes, such as provided by the present invention, are valuable as potential targets for the development of therapeutics to treat these and other diseases/disorders. Furthermore, SNPs in cytokine receptor genes, such as provided by the present invention, may serve as valuable markers for the diagnosis, prognosis, prevention, and/or treatment of such diseases/disorders.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

Receptor proteins, particularly members of the cytokine receptor subfamily, are a major target for drug action and development. Accordingly, it is valuable to the field of pharmaceutical development to identify and characterize previously unknown members of this subfamily of receptor proteins. The present invention advances the state of the art by providing previously unidentified human receptor proteins that have homology to members of the cytokine receptor subfamily.

SUMMARY OF THE INVENTION

The present invention is based in part on the identification of amino acid sequences of human receptor peptides and proteins that are related to the cytokine receptor subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate receptor activity in cells and tissues that express the receptor. Experimental data as provided in FIG. 1 indicates expression in the placenta, marrow, liver/spleen, and in leukocytes.

DESCRIPTION OF THE FIGURE SHEETS

FIGS. 1A and 1B provide the nucleotide sequence of a cDNA molecule that encodes the receptor protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the placenta, marrow, liver/spleen, and in leukocytes.

FIGS. 2A to 2C provide the predicted amino acid sequence of the receptor of the present invention. (SEQ ID NO:2) In addition structure and functional information such as protein family, function, and modification sites is provided where available, allowing one to readily determine specific uses of inventions based on this molecular sequence.

FIGS. 3A to 3L genomic sequences that span the gene encoding the receptor protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 25 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a receptor protein or part of a receptor protein and are related to the cytokine receptor subfamily. Utilizing these sequences, additional genomic sequences were assembled and transcript and/or cDNA sequences were isolated and characterized. Based on this analysis, the present invention provides amino acid sequences of human receptor peptides and proteins that are related to the cytokine receptor subfamily, nucleic acid sequences in the form of transcript sequences, cDNA sequences and/or genomic sequences that encode these receptor peptides and proteins, nucleic acid variation (allelic information), tissue distribution of expression, and information about the closest art known protein/peptide/domain that has structural or sequence homology to the receptor of the present invention.

In addition to being previously unknown, the peptides that are provided in the present invention are selected based on their ability to be used for the development of commercially important products and services. Specifically, the present peptides are selected based on homology and/or structural relatedness to known receptor proteins of the cytokine receptor subfamily and the expression pattern observed. Experimental data as provided in FIGS. 1A and 1B indicates expression in the placenta, marrow, liver/spleen, and in leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known cytokine family or subfamily of receptor proteins.

Specific Embodiments

Peptide Molecules

The present invention provides nucleic acid sequences that encode protein molecules that have been identified as being members of the receptor family of proteins and are related to the cytokine receptor subfamily (protein sequences are provided in FIGS. 2A to 2C transcript/cDNA sequences are provided in FIGS. 1A and 1B and genomic sequences are provided in FIGS. 3A to 3L. The peptide sequences provided in FIGS. 2A to 2C as well as the obvious variants described herein, particularly allelic variants as identified herein and using the information in FIGS. 3A to 3L will be referred herein as the receptor peptides of the present invention, receptor peptides, or peptides/proteins of the present invention.

The present invention provides isolated peptide and protein molecules that consist of, consist essentially of, or comprise the amino acid sequences of the receptor peptides disclosed in the FIGS. 2A to 2C (encoded by the nucleic acid molecule shown in FIGS. 1A and 1B transcript/cDNA or FIGS. 3A and 3L genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the receptor peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated receptor peptide can be purified from cells that naturally express it, purified from cells that have been altered to express it (recombinant), or synthesized using known protein synthesis methods. Experimental data as provided in FIG. 1 indicates expression in the placenta, marrow, liver/spleen, and in leukocytes. For example, a nucleic acid molecule encoding the receptor peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIGS. 2A to 2C (SEQ ID NO:2), for example, proteins encoded by the transcript/cDNA nucleic acid sequences shown in FIGS. 1A and 1B (SEQ ID NO:1) and the genomic sequences provided in FIGS. 3A to 3L (SEQ ID NO:3). The amino acid sequence of such a protein is provided in FIGS. 2A to 2C protein consists of an amino acid sequence when the amino acid sequence is the final amino acid sequence of the protein.

The present invention further provides proteins that consist essentially of the amino acid sequences provided in FIGS. 2A to 2C (SEQ ID NO:2), for example, proteins encoded by the transcript/cDNA nucleic acid sequences shown in FIGS. 1A and 1B (SEQ ID NO:1) and the genomic sequences provided in FIGS. 3A to 3L (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIGS. 2A to 2C (SEQ ID NO:2), for example, proteins encoded by the transcript/cDNA nucleic acid sequences shown in FIGS. 1A and 1B (SEQ ID NO:1) and the genomic sequences provided in FIGS. 3A to 3L (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the receptor peptides of the present invention are the naturally occurring mature proteins. A brief description of how various types of these proteins can be made/isolated is provided below.

The receptor peptides of the present invention can be attached to heterologous sequences to form chimeric or fusion proteins. Such chimeric and fusion proteins comprise a receptor peptide operatively linked to a heterologous protein having an amino acid sequence not substantially homologous to the receptor peptide. "Operatively linked" indicates that the receptor peptide and the heterologous protein are fused in-frame. The heterologous protein can be fused to the N-terminus or C-terminus of the receptor peptide.

In some uses, the fusion protein does not affect the activity of the receptor peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant receptor peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A receptor peptide-encoding nucleic acid can be cloned into such an expression vector such that the fusion moiety is linked in-frame to the receptor peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the receptor peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM 120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the receptor peptides of the present invention as well as being encoded by the same genetic locus as the receptor peptide provided herein. The gene encoding the novel receptor protein of the present invention is located on a genome component that has been mapped to human chromosome 22 (as indicated in FIG. 3), which is supported by multiple lines of evidence, such as STS and BAC map data.

Allelic variants of a receptor peptide can readily be identified as being a human protein having a high degree (significant) of sequence homology/identity to at least a portion of the receptor peptide as well as being encoded by the same genetic locus as the receptor peptide provided herein. Genetic locus can readily be determined based on the genomic information provided in FIG. 3, such as the genomic sequence mapped to the reference human. The gene encoding the novel receptor protein of the present invention is located on a genome component that has been mapped to human chromosome 22 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a receptor peptide encoding nucleic acid molecule under stringent conditions as more fully described below.

FIGS. 3A to 3L provide information on SNPs that have been found in the gene encoding the receptor protein of the present invention. SNPs were identified at 25 different nucleotide positions. Some of these SNPs that are located outside the ORF and in introns may affect gene expression.

Paralogs of a receptor peptide can readily be identified as having some degree of significant sequence homology/identity to at least a portion of the receptor peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a receptor peptide encoding nucleic acid molecule under moderate to stringent conditions as more fully described below.

Orthologs of a receptor peptide can readily be identified as having some degree of significant sequence homology/identity to at least a portion of the receptor peptide as well as being encoded by a gene from another organism. Preferred orthologs will be isolated from mammals, preferably primates, for the development of human therapeutic targets and agents. Such orthologs will be encoded by a nucleic acid sequence that will hybridize to a receptor peptide encoding nucleic acid molecule under moderate to stringent conditions, as more fully described below, depending on the degree of relatedness of the two organisms yielding the proteins.

Non-naturally occurring variants of the receptor peptides of the present invention can readily be generated using recombinant techniques. Such variants include, but are not limited to deletions, additions and substitutions in the amino acid sequence of the receptor peptide. For example, one class of substitutions are conserved amino acid substitution. Such substitutions are those that substitute a given amino acid in a receptor peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant receptor peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIGS. 2A to 2C provide the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as receptor activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the receptor peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a receptor peptide. Such fragments can be chosen based on the ability to retain one or more of the biological activities of the receptor peptide or could be chosen for the ability to perform a function, e.g. bind a substrate or act as an immunogen.

Particularly important fragments are biologically active fragments, peptides that are, for example, about 8 or more amino acids in length. Such fragments will typically comprise a domain or motif of the receptor peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIGS. 2A to 2C.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in receptor peptides are described in basic texts, detailed monographs, and the research literature, and they are well known to those of skill in the art (some of these features are identified in FIGS. 2A to 2C.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W.H. Freeman and Company, New York (1993). Many detailed reviews are available on this subject, such as by Wold, F., *Posttranslational Covalent Modification of proteins*, B. C. Johnson, Ed., Academic Press, New York 1–12 (1983); Seifter et al. (*Meth. Enzymol*. 182: 626–646 (1990)) and Rattan et al. (*Ann. N.Y Acad Sci*.663:48–62 (1992)).

Accordingly, the receptor peptides of the present invention also encompass derivatives or analogs in which a substituted amino acid residue is not one encoded by the genetic code, in which a substituent group is included, in which the mature receptor peptide is fused with another compound, such as a compound to increase the half-life of the receptor peptide (for example, polyethylene glycol), or in which the additional amino acids are fused to the mature receptor peptide, such as a leader or secretory sequence or a sequence for purification of the mature receptor peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a receptor-effector protein interaction or receptor-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, receptors isolated from humans and their human/mammalian orthologs serve as targets for identifying agents for use in mammalian therapeutic applications, e.g. a human drug, particularly in modulating a biological or pathological response in a cell or tissue that expresses the receptor. Experimental data as provided in FIGS. 1A and 1B indicates that receptor proteins of the present invention are expressed in the placenta, marrow, and liver/spleen, as indicated by virtual northern blot analysis. In addition, PCR-based tissue screening panels indicates expression in human leukocytes. A large percentage of pharmaceutical agents are being developed that modulate the activity of receptor proteins, particularly members of the cytokine subfamily (see Background of the Invention). The structural and functional information provided in the Background and Figures provide specific and substantial uses for the molecules of the present invention, particularly in combination with the expression information provided in FIGS. 1A and 1B Experimental data as provided in FIG. 1 indicates expression in the placenta, marrow, liver/spleen, and in leukocytes. Such uses can readily be determined using the information provided herein, that which is known in the art, and routine experimentation.

The proteins of the present invention (including variants and fragments that may have been disclosed prior to the present invention) are useful for biological assays related to receptors that are related to members of the cytokine subfamily. Such assays involve any of the known receptor functions or activities or properties useful for diagnosis and treatment of receptor-related conditions that are specific for the subfamily of receptors that the one of the present invention belongs to, particularly in cells and tissues that express the receptor. Experimental data as provided in FIGS. 1A and 1B indicates that receptor proteins of the present invention are expressed in the placenta, marrow, and liver/spleen, as indicated by virtual northern blot analysis. In addition, PCR-based tissue screening panels indicates expression in human leukocytes.

The proteins of the present invention are also useful in drug screening assays, in cell-based or cell-free systems. Cell-based systems can be native, i.e., cells that normally express the receptor, as a biopsy or expanded in cell culture.

Experimental data as provided in FIG. 1 indicates expression in the placenta, marrow, liver/spleen, and in leukocytes. In an alternate embodiment, cell-based assays involve recombinant host cells expressing the receptor protein.

The polypeptides can be used to identify compounds that modulate receptor activity of the protein in its natural state or an altered form that causes a specific disease or pathology associated with the receptor. Both the receptors of the present invention and appropriate variants and fragments can be used in high-throughput screens to assay candidate compounds for the ability to bind to the receptor. These compounds can be further screened against a functional receptor to determine the effect of the compound on the receptor activity. Further, these compounds can be tested in animal or invertebrate systems to determine activity/effectiveness. Compounds can be identified that activate (agonist) or inactivate (antagonist) the receptor to a desired degree.

Further, the proteins of the present invention can be used to screen a compound for the ability to stimulate or inhibit interaction between the receptor protein and a molecule that normally interacts with the receptor protein, e.g. an extracellular binding ligand or a component of the signal pathway that the receptor protein normally interacts (for example, a cytosolic signal protein). Such assays typically include the steps of combining the receptor protein with a candidate compound under conditions that allow the receptor protein, or fragment, to interact with the target molecule, and to detect the formation of a complex between the protein and the target or to detect the biochemical consequence of the interaction with the receptor protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant receptors or appropriate fragments containing mutations that affect receptor function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) receptor activity. The assays typically involve an assay of events in the signal transduction pathway that indicate receptor activity. Thus, the phosphorylation of a substrate, activation of a protein, a change in the expression of genes that are up- or down-regulated in response to the receptor protein dependent signal cascade can be assayed.

Any of the biological or biochemical functions mediated by the receptor can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the receptor can be assayed. Experimental data as provided in FIG. 1 indicates that receptor proteins of the present invention are expressed in the placenta, marrow, and liver/spleen, as indicated by virtual northern blot analysis. In addition, PCR-based tissue screening panels indicates expression in human leukocytes.

Binding and/or activating compounds can also be screened by using chimeric receptor proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native receptor. Accordingly, a different set of signal transduction components is available as an end-point assay for activation. This allows for assays to be performed in other than the specific host cell from which the receptor is derived.

The proteins of the present invention are also useful in competition binding assays in methods designed to discover compounds that interact with the receptor (e.g. binding partners and/or ligands). Thus, a compound is exposed to a receptor polypeptide under conditions that allow the compound to bind or to otherwise interact with the polypeptide. Soluble receptor polypeptide is also added to the mixture. If the test compound interacts with the soluble receptor polypeptide, it decreases the amount of complex formed or activity from the receptor target. This type of assay is particularly useful in cases in which compounds are sought that interact with specific regions of the receptor. Thus, the soluble polypeptide that competes with the target receptor region is designed to contain peptide sequences corresponding to the region of interest.

To perform cell free drug screening assays, it is sometimes desirable to immobilize either the receptor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of receptor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a receptor-binding protein and a candidate compound are incubated in the receptor protein-presenting wells and the amount of complex trapped in the well can be quantitated. Methods for detecting such complexes, in addition to those described above for the GST-immobilized complexes, include immunodetection of complexes using antibodies reactive with the receptor protein target molecule, or which are reactive with receptor protein and compete with the target molecule, as well as enzyme-linked assays which rely on detecting an enzymatic activity associated with the target molecule.

Agents that modulate one of the receptors of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of receptor protein activity identified according to these drug screening assays can be used to treat a subject with a disorder mediated by the receptor pathway, by treating cells or tissues that express the receptor. Experimental data as provided in FIGS. 1A and 1B indicates expression in the placenta, marrow, liver/spleen, and in leukocytes. These methods of treatment include the steps of administering a modulator of receptor activity in a pharmaceutical composition to a subject in need of such treatment, the modulator being identified as described herein.

In yet another aspect of the invention, the receptor proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1 993) *Biotechniques* 14:920–924; Iwabuchi et al (1993) *Oncogene* 8:1693–1696; and Brent WO94/10300), to identify other proteins, which bind to or interact with the receptor and are involved in receptor activity. Such receptor-binding proteins are also likely to be involved in the propagation of signals by the receptor proteins or receptor targets as, for example, downstream elements of a receptor-mediated signaling pathway. Alternatively, such receptor-binding proteins are likely to be receptor inhibitors.

The two-hybrid system is based on the modular nature of most transcription factors, which consist of separable DNA-binding and activation domains. Briefly, the assay utilizes two different DNA constructs. In one construct, the gene that codes for a receptor protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a receptor-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the receptor protein.

This invention further pertains to novel agents identified by the above-described screening assays. Accordingly, it is within the scope of this invention to further use an agent identified as described herein in an appropriate animal model. For example, an agent identified as described herein (e.g., a receptor-modulating agent, an antisense receptor nucleic acid molecule, a receptor-specific antibody, or a receptor-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The receptor proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the placenta, marrow, liver/spleen, and in leukocytes. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and receptor activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the placenta, marrow, liver/spleen, and in leukocytes. Accordingly, methods for treatment include the use of the receptor protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the receptor proteins. Antibodies can be prepared from any region of the peptide as described herein. However, preferred regions will include those involved in function/activity and/or receptor/binding partner interaction. FIGS. 2A to 2C can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIGS. 2A to 2C.

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that receptor proteins of the present invention are expressed in the placenta, marrow, and liver/spleen, as indicated by virtual northern blot analysis. In addition, PCR-based tissue screening panels indicates expression in human leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the placenta, marrow, liver/spleen, and in leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the placenta, marrow, liver/spleen, and in leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the placenta, marrow, liver/spleen, and in leukocytes. Thus, where a specific protein has been correlated with expression in a specific tissue, antibodies that are specific for this protein can be used to identify a tissue type.

The antibodies are also useful for inhibiting protein function, for example, blocking the binding of the receptor peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a receptor peptide or protein of the present invention (cDNA, transcript and genomic sequence). Such nucleic acid molecules will consist of, consist essentially of, or comprise a nucleotide sequence that encodes one of the receptor peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of , the nucleotide sequence shown in FIGS. 1A and 1B (SEQ ID NO:1, transcript sequence and SEQ ID NO:3, genomic sequence), or any nucleic acid molecule that encodes the protein provided in FIGS. 2A to 2C SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIGS. 1A and 1B (SEQ ID NO:1, transcript sequence and SEQ ID NO:3, genomic sequence), or any nucleic acid molecule that encodes the protein provided in FIGS. 2A to 2C SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIGS. 1A and 1B (SEQ ID NO: 1, transcript sequence and SEQ ID NO:3, genomic sequence), or any nucleic acid molecule that encodes the protein provided in FIGS. 2A to 2C SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1A and 1B and 3A to 3L both coding and non-coding sequences are provided. Because of the source of the present invention, humans genomic sequence (FIGS. 3A to 3L) and cDNA/transcript sequences (FIGS. 1A and 1B), the nucleic acid molecules in the Figures will contain genomic intronic sequences, 5' and 3' non-coding sequences, gene regulatory regions and non-coding intergenic sequences. In general such sequence features are either noted in FIGS. 1A and 1B and 3A to 3L or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the receptor peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the receptor proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1A and 1B and 3A to 3L. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIGS. 3A to 3L.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel receptor protein of the present invention is located on a genome component that has been mapped to human chromosome 22 (as indicated in FIGS. 3A to 3L), which is supported by multiple lines of evidence, such as STS and BAC map data.

FIGS. 3A to 3L provide information on SNPs that have been found in the gene encoding the receptor protein of the present invention. SNPs were identified at 25 different nucleotide positions. Some of these SNPs that are located outside the ORF and in introns may affect gene expression.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIGS. 2A to 2C and to isolate cDNA and genomic clones that correspond to variants (alleles, orthologs, etc.) producing the same or related peptides shown in FIGS. 2A to 2C. As illustrated in FIGS. 3A to 3L SNPs were identified at 25 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel receptor protein of the present invention is located on a genome component that has been mapped to human chromosome 22 (as indicated in FIGS. 3A to 3L, which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that receptor proteins of the present invention are expressed in the placenta, marrow, and liver/spleen, as indicated by virtual northern blot analysis. In addition, PCR-based tissue screening panels indicates expression in human leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in receptor protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a receptor protein, such as by measuring a level of a receptor-encoding nucleic acid in a sample of cells from a subject e.g., mRNA or genomic DNA, or determining if a receptor gene has been mutated. Experimental data as provided in FIGS. 1A and 1 indicates that receptor proteins of the present invention are expressed in the placenta, marrow, and liver/spleen, as indicated by virtual northern blot analysis. In addition, PCR-based tissue screening panels indicates expression in human leukocytes.

Nucleic acid expression assays are useful for drug screening to identify compounds that modulate receptor nucleic acid expression.

The invention thus provides a method for identifying a compound that can be used to treat a disorder associated with nucleic acid expression of the receptor gene, particularly biological and pathological processes that are mediated by the receptor in cells and tissues that express it. Experimental data as provided in FIGS. 1A and 1B indicates expression in the placenta, marrow, liver/spleen, and in leukocytes. The method typically includes assaying the ability of the compound to modulate the expression of the receptor nucleic acid and thus identifying a compound that can be used to treat a disorder characterized by undesired receptor nucleic acid expression. The assays can be performed in cell-based and cell-free systems. Cell-based assays include cells naturally expressing the receptor nucleic acid or recombinant cells genetically engineered to express specific nucleic acid sequences.

The assay for receptor nucleic acid expression can involve direct assay of nucleic acid levels, such as mRNA levels, or on collateral compounds involved in the signal pathway. Further, the expression of genes that are up- or down-regulated in response to the receptor protein signal pathway can also be assayed. In this embodiment the regulatory regions of these genes can be operably linked to a reporter gene such as luciferase.

Thus, modulators of receptor gene expression can be identified in a method wherein a cell is contacted with a candidate compound and the expression of mRNA determined. The level of expression of receptor mRNA in the presence of the candidate compound is compared to the level of expression of receptor mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate receptor nucleic acid expression in cells and tissues that express the receptor. Experimental data as provided in FIG. 1 indicates that receptor proteins of the present invention are expressed in the placenta, marrow, and liver/spleen, as indicated by virtual northern blot analysis. In addition, PCR-based tissue screening panels indicates expression in human leukocytes. Modulation includes both up-regulation (i.e. activation or agonization) or down-regulation (suppression or antagonization) or nucleic acid expression.

Alternatively, a modulator for receptor nucleic acid expression can be a small molecule or drug identified using the screening assays described herein as long as the drug or small molecule inhibits the receptor nucleic acid expression in the cells and tissues that express the protein. Experimental data as provided in FIG. 1 indicates expression in the placenta, marrow, liver/spleen, and in leukocytes.

The nucleic acid molecules are also useful for monitoring the effectiveness of modulating compounds on the expression or activity of the receptor gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in receptor nucleic acid expression, and particularly in qualitative changes that lead to pathology. The nucleic acid molecules can be used to detect mutations in receptor genes and gene expression products such as mRNA. The nucleic acid molecules can be used as hybridization probes to detect naturally occurring genetic mutations in the receptor gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the receptor gene associated with a dysfunction provides a diagnostic tool for an active disease or susceptibility to disease when the disease results from overexpression, underexpression, or altered expression of a receptor protein.

Individuals carrying mutations in the receptor gene can be detected at the nucleic acid level by a variety of techniques. FIGS. 3A to 3L provide information on SNPs that have been found in the gene encoding the receptor protein of the present invention. SNPs were identified at 25 different nucleotide positions. Some of these SNPs that are located outside the ORF and in introns may affect gene expression. The gene encoding the novel receptor protein of the present invention is located on a genome component that has been mapped to human chromosome 22 (as indicated in FIGS. 3A to 3L, which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a receptor gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant receptor gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the receptor gene in an individual in order to select an appropriate compound or dosage regimen for treatment. FIGS. 3A to 3L provide information on SNPs that have been found in the gene encoding the receptor protein of the present invention. SNPs were identified at 25 different nucleotide positions. Some of these SNPs that are located outside the ORF and in introns may affect gene expression.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control receptor gene expression in cells, tissues, and organisms. A DNA antisense nucleic acid molecule is designed to be complementary to a region of the gene involved in transcription, preventing transcription and hence production of receptor protein. An antisense RNA or DNA nucleic acid molecule would hybridize to the mRNA and thus block translation of mRNA into receptor protein.

Alternatively, a class of antisense molecules can be used to inactivate mRNA in order to decrease expression of receptor nucleic acid. Accordingly, these molecules can treat a disorder characterized by abnormal or undesired receptor nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the receptor protein, such as substrate binding.

The nucleic acid molecules also provide vectors for gene therapy in patients containing cells that are aberrant in receptor gene expression. Thus, recombinant cells, which include the patient's cells that have been engineered ex vivo and returned to the patient, are introduced into an individual where the cells produce the desired receptor protein to treat the individual.

The invention also encompasses kits for detecting the presence of a receptor nucleic acid in a biological sample. Experimental data as provided in FIG. 1 indicates that receptor proteins of the present invention are expressed in the placenta, marrow, and liver/spleen, as indicated by virtual northern blot analysis. In addition, PCR-based tissue screening panels indicates expression in human leukocytes. For example, the kit can comprise reagents such as a labeled or labelable nucleic acid or agent capable of detecting receptor nucleic acid in a biological sample; means for determining the amount of receptor nucleic acid in the sample; and means for comparing the amount of receptor nucleic acid in the sample with a standard. The compound or agent can be packaged in a suitable container. The kit can further comprise instructions for using the kit to detect receptor protein mRNA or DNA.

Nucleic Acid Arrays

The present invention further provides nucleic acid detection kits, such as arrays or microarrays of nucleic acid molecules that are based on the sequence information provided in FIGS. 1A and 1B and 3A to 3L (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the receptor proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the receptor gene of the present invention. FIGS. 3A to 3L provide information on SNPs that have been found in the gene encoding the receptor protein of the present invention. SNPs were identified at 25 different nucleotide positions. Some of these SNPs that are located outside the ORF and in introns may affect gene expression.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified receptor gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers.

Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning. A Laboratory Manual*. 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroreceptor. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al, *Gene* 69:301–315 (1988)) and pET 11 d (Studier et al., *Gene Expression Technology. Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res*. 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kurjan et al, *Cell* 30:933–943(1982)), pJRY88 (Schultz et al, *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol*. 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mamalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as receptors, appropriate secretion signals are incorporated into the vector. The signal sequence can be endogenous to the peptides or heterologous to these peptides.

Where the peptide is not secreted into the medium, which is typically the case with receptors, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a receptor protein or peptide that can be further purified to produce desired amounts of receptor protein or fragments. Thus, host cells containing expression vectors are useful for peptide production.

Host cells are also useful for conducting cell-based assays involving the receptor protein or receptor protein fragments, such as those described above as well as other formats known in the art. Thus, a recombinant host cell expressing a native receptor protein is useful for assaying compounds that stimulate or inhibit receptor protein function.

Host cells are also useful for identifying receptor protein mutants in which these functions are affected. If the mutants naturally occur and give rise to a pathology, host cells containing the mutations are useful to assay compounds that have a desired effect on the mutant receptor protein (for example, stimulating or inhibiting function) which may not be indicated by their effect on the native receptor protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a receptor protein and identifying and evaluating modulators of receptor protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the receptor protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the receptor protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, receptor protein activation, and signal transduction, may not be evident from in vitro cell-free or cell-based assays. Accordingly, it is useful to provide non-human transgenic animals to assay in vivo receptor protein function, including substrate interaction, the effect of specific mutant receptor proteins on receptor protein function and substrate interaction, and the effect of chimeric receptor proteins. It is also possible to assess the effect of null mutations, that is, mutations that substantially or completely eliminate one or more receptor protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising SEQ ID NO:2, the process comprising culturing the host cell of claim 3 under conditions sufficient for the production of said polypeptide, and recovering said polypeptide.

5. The vector of claim 2, wherein said vector is selected from the group consisting of a plasmid, a virus, and a bacteriophage.

6. The vector of claim 2, wherein said isolated nucleic acid molecule encodes a polypeptide comprising SEQ ID NO:2 and is inserted into said vector in proper orientation and correct reading frame such that a polypeptide comprising SEQ ID NO:2 may be expressed by a cell transformed with said vector.

7. The vector of claim 6, wherein said isolated nucleic acid molecule is operatively linked to a promoter sequence.

8. An isolated polynucleotide consisting of the nucleotide sequence of SEQ ID NO:1.

9. An isolated polynucleotide consisting of the nucleotide sequence of SEQ ID NO:3.

* * * * *